US009078874B2

(12) United States Patent
Potier et al.

(10) Patent No.: US 9,078,874 B2
(45) Date of Patent: Jul. 14, 2015

(54) COMPOSITION AND METHOD FOR TREATING COGNITIVE IMPAIRMENTS IN DOWN SYNDROM SUBJECTS

(75) Inventors: Marie-Caude Potier, Asnieres-sur-Seine (FR); Robert Dodd, Paris (FR); Benoît Delatour, Cachan (FR); Jérôme Braudeau, Yerres (FR); Yann Herault, Illkirch (FR)

(73) Assignee: Centre National De La Recherche Scientifique—CNRS, Paris (FR)

( * ) Notice: Subject to any disclaimer, the term of this patent is extended or adjusted under 35 U.S.C. 154(b) by 89 days.

(21) Appl. No.: 13/392,044

(22) PCT Filed: Aug. 24, 2010

(86) PCT No.: PCT/IB2010/053796
§ 371 (c)(1),
(2), (4) Date: Jul. 3, 2012

(87) PCT Pub. No.: WO2011/024115
PCT Pub. Date: Mar. 3, 2011

(65) Prior Publication Data
US 2012/0283248 A1 Nov. 8, 2012

Related U.S. Application Data

(60) Provisional application No. 61/236,625, filed on Aug. 25, 2009.

(30) Foreign Application Priority Data

Aug. 25, 2009 (EP) .................................. 09290643

(51) Int. Cl.
| | | |
|---|---|---|
| *A61P 25/28* | (2006.01) | |
| *A61K 31/381* | (2006.01) | |
| *A61K 9/00* | (2006.01) | |
| *A61K 31/4162* | (2006.01) | |
| *A61K 31/502* | (2006.01) | |
| *A61K 31/5517* | (2006.01) | |

(52) U.S. Cl.
CPC ............. *A61K 31/381* (2013.01); *A61K 9/0019* (2013.01); *A61K 31/4162* (2013.01); *A61K 31/502* (2013.01); *A61K 31/5517* (2013.01)

(58) Field of Classification Search
CPC ........... A61K 31/5517; A61K 31/5025; A61K 31/427
USPC ................... 540/494, 555; 544/234; 548/202; 514/219, 248, 365
See application file for complete search history.

(56) References Cited

U.S. PATENT DOCUMENTS

| 6,262,103 B1 * | 7/2001 | Broughton et al. ........... 514/406 |
| 7,514,426 B2 * | 4/2009 | Knust et al. ................... 514/219 |
| 2006/0084642 A1 | 4/2006 | Knust et al. |

FOREIGN PATENT DOCUMENTS

| WO | WO 96/25948 A1 | 8/1996 |
| WO | WO 01/38331 A2 | 5/2001 |
| WO | WO 03/006471 A1 | 1/2003 |

OTHER PUBLICATIONS

A. C. Costa et al., "Behavioral validation of the Ts65Dn mouse model for Down syndrome of a genetic background free of the retinal degeneration mutation Pdeb(rd1)", Behav. Brain Res. 206, 52-62 (2010).
A. El Hadri et al., "N-Substituted 4-Amino-3,3-dipropyl-2(3H)-furanones: New Positive Allosteric Modulators of the GABA(A) Receptor Sharing Electrophysiological Properties with the Anticonvulsant Loreclezole", J. Med. Chem. 45, 2824-2831 (2002).
Atack et al., "L-655,708 enhances cognition in rats but is not proconvulsant at a dose selective for alpha5-containing GABA(A) receptors", Neuropharmacology, 51:1023-1029 (2006).
Atack, J. R.; "Preclinical and clinical pharmacology of the GABA(A) receptor alpha5 subtype-selective inverse agonist alpha5IA", Pharmacol. Ther. 125(1):11-26 (2010).
Ballard et al., "RO4938581, a novel congnitive enhancer acting at GABA(A) alpha5 subunit-containing receptors", Psychopharmacology, 202:207-223 (2009).
Best, T. K. et al. "Ts65Dn, a Mouse Model of Down Syndrome, Exhibits Increased GABA(B)-Induced Potassium Current", J. Neurophysiol. 97, 892-900 (2007).
Chambers et al., "An Orally Bioavailable, Functionally Selective Inverse Agonist at the Benzodiazepine Site of GABA(A) alpha5 Receptors with Cognition Enhancing Properties", J. Med. Chem., 47:5829-5832 (2004).
Collinson et al., "An inverse agonist selective for alpha5 subunit-containing GABA(A) receptors improves encoding and recall but not consolidation in the Morris water maze", Psychopharmacology, 188:619-628 (2006).
Collinson et al., "Enhanced Learning and Memory and Altered GABAergic Synaptic Transmission in Mice Lacking the alpha5 Subunit of the GABA(A) Receptor", J. Neurosci., 22(13):5572-5580 (2002).

(Continued)

*Primary Examiner* — Bruck Kifle
(74) *Attorney, Agent, or Firm* — Arent Fox LLP

(57) ABSTRACT

Compounds having inverse agonist functional selectivity for GABA$_A$ receptors containing the α5 subunit for use as a medicament in the treatment of cognitive impairments in subjects suffering from Down syndrome. The use of these compounds is disclosed. Pharmaceutical compositions for such treatment can comprise these compounds or suitable pharmaceutically acceptable salt thereof, a polyethoxylated castor oil and dimethyl sulfoxide (DMSO). Methods are disclosed for enhancing cognitive function, or treating or lessening the severity of cognitive impairments, in subjects suffering from Down syndrome by administering to a subject in need thereof a pharmaceutically effective amount of one or more of these compounds.

11 Claims, 16 Drawing Sheets

(56) References Cited

OTHER PUBLICATIONS

Costa A. C. S. et al., "Deficits in hippocampal CA1 LTP induced by TBS but not HFS in the Ts65Dn mouse: A model of Down syndrome", Neurosci. Lett., vol. 382, No. 3, pp. 317-322 (2005).
D. J. Moura et al., "Effects of beta-carboline alkaloids on the object recognition task in mice", Life Sci. 79, 2099-2104 (2006).
Dawson et al., "An Inverse Agonist Selective for alpha5 Subunit-Containing GABA(A) Receptors Enhances Cognition", The Journal of Pharmacology and Experimental Therapeutics, 316(3):1335-1345 (2006).
Demas, G. E. et at, "Spatial memory deficits in segmental trisomic Ts65Dn mice", Behav. Brain Res., 82, 85-92 (1996).
D'Hulst, C. et al., "The complexity of the GABA(A) receptor shapes unique pharmacological profiles", Drug Discov. Today, 14(17/18), 866-875 (2009).
Escorihuela. R. M. et al., "A behavioral assessment of Ts65Dn mice: a putative Down syndrome model."Neurosci. Lett., 199, 143-146 (1995).
F. Fernandez et al., "Pharmacotherapy for cognitive impairment in a mouse model of Down syndrome," Nature Neuroscience, 10(4):411-413 (2007).
Hoffman, G. E. et al., "C-Fos and Fos-Related Antigens as Markers for Neuronal Activity: Perspectives From Neuroendocrine Systems" NIDA Res. Monogr, 125, 117-133 (1993).
International Search Report dated Nov. 19, 2010 issued in International Patent Application No. PCT/IB2010/053796.
Kleschevnikov A. M., et al., "Hippocampal Long-Term Potentiation Suppressed by Increased Inhibition in the Ts65Dn Mouse, a Genetic Model of Down Syndrome", The Journal of Neuroscience, 24(37):8153-8160 (2004).
Lobaugh N. J. et al., "Piracetam Therapy Does Not Enhance Cognitive Functioning In Children With Down Syndrome", Arch. Pediatr. Adolesc. Med.; 155(4):442-448 (2001).
McNamara R. K. et al., "Benzodiazepine receptor antagonists flumazenil and CGS 8216 and inverse-agonist beta-CCM enhance spatial learning in the rat: Dissociation from anxiogenic actions", Psychobiology, 21(2):101-108 (1993).

Nutt D. J. et al., "Blockade of alcohol's amnestic activity in humans by an alpha5 subtype benzodiazepine receptor inverse agonist", Neuropharmacology, 53:810-820 (2007).
Palop et al., "Aberrant Excitatory Neuronal Activity and Compensatory Remodeling of Inhibitory Hippocampal Circuits in Mouse Models of Alzheimer's Disease." Neuron. 55(5):697-711 (2007).
Reeves et al., "A mouse model for Down syndrome exhibits learning and baviour deficits", Nature Genetics, 11(2):177-184 (1995).
Rueda, N. et al., "Chronic pentylenetetrazole but not donepezil treatment rescues spatial cognition in Ts65Dn mice, a model for Down syndrome", Neurosci. Lett. 433, 22-27 (2008).
S. A. Merschman et al., "Characterization of the solubility of a poorly soluble hydroxylated metabolite in human urine and its implications for potential renal toxicity", Pharmazie 60, 359-363 (2005).
S. M. Hoelter et al., "Sighted C3H' mice—a tool for analysing the influence of vision on mouse behaviour?" Front Biosci. 13, 5810-5823 (2008).
Schmitt, "Neuro-modulation, aminergic neuro-disinhibition and neuro-degeneration. Draft of a comprehensive theory for Alzheimer disease", Med. Hypotheses.;65(6):1106-1119 (2005).
Sherman, S. L. et al., "Epidemiology of Down Syndrome", Ment. Retard. Dev. Disabil. Res. Rev. 13, 221-227 (2007).
Siarey, R. J. et. al, "Altered Long-term Potentiation in the Young and Old Ts65Dn Mouse, a Model for Down Syndrome", Neuropharmacology 36, 1549-1554 (1997).
Siarey, R.J. et al., "Increased synaptic depression in the Ts65Dn mouse, a model for mental retardation in Down syndrome", Neuropharmacology, 38, 1917-1920 (1999).
Sperk, G. et al., "GABA(A) Receptor Subunits in the Rat Hippocampus I: Immunocytochemical Distribution of 13 Subunits", Neuroscience 80, 987-1000 (1997).
Sternfeld et al., "Selective, Orally Active Gamma-Aminobutyric Acid(A) alpha5 Receptor Inverse Agonists as Cognition Enhancers", J. Med. Chem., 47:2176-2179 (2004).
Sur, C. et al., "Rat and Human Hippocampal alpha5 Subunit-Containing gamma-Aminobutyric Acid(A) Receptors Have alpha5beta3gamma2 Pharmacological Characteristics", Mol. Pharmacol. 54: 928-933 (1998).
Venault et al., "Benzodiazepine impairs and beta-carboline enhances performance in learning and memory tasks", Nature, 321(6073):864-866 (1986).

* cited by examiner

| Structures | Genotype | treatment | surface ratios | Drug effect | Gen. effect | Drug x Gen interaction |
|---|---|---|---|---|---|---|
| PRh | Euploids | placebo | 0,68% ±0,16 | p = 0,02 | NS | NS |
| | | GABA-1A | 1,12% ±0,09 | | | |
| | Ts65Dn | placebo | 0,57% ±0,1 | | | |
| | | GABA-1A | 0,97% ±0,22 | | | |
| GD | Euploids | placebo | 0,91% ±0,1 | NS | NS | NS |
| | | GABA-1A | 1,12% ±0,19 | | | |
| | Ts65Dn | placebo | 1,32% ±0,33 | | | |
| | | GABA-1A | 1,45% ±0,13 | | | |
| CA1 | Euploids | placebo | 1,45% ±0,34 | p = 0,03 | NS | NS |
| | | GABA-1A | 2,72% ±0,63 | | | |
| | Ts65Dn | placebo | 1,16% ±0,14 | | | |
| | | GABA-1A | 2,13% ±0,19 | | | |
| Post. Cing. | Euploids | placebo | 0,78% ±0,27 | p = 0,0001 | NS | NS |
| | | GABA-1A | 2,16% ±0,22 | | | |
| | Ts65Dn | placebo | 1,04% ±0,29 | | | |
| | | GABA-1A | 2,65% ±0,16 | | | |

FIGURE 14

COMPOSITION AND METHOD FOR TREATING COGNITIVE IMPAIRMENTS IN DOWN SYNDROM SUBJECTS

CROSS-REFERENCE TO RELATED APPLICATIONS

This application is a National Stage entry of International Application No. PCT/IB2010/053796, filed Aug. 24, 2010, which claims priority to European Application No. 09290643.7, filed Aug. 25, 2009 and U.S. Patent Application No. 61/236,625, filed Aug. 25, 2009. The disclosures of the prior applications are incorporated in their entirety by reference.

FIELD OF THE INVENTION

This application relates to compounds having inverse agonist functional selectivity for $GABA_A$ receptors containing the α5 subunit for use as a medicament in the treatment of cognitive impairments in subjects suffering from Down syndrome. The present application also relates to the use of compounds having inverse agonist functional selectivity for $GABA_A$ receptors containing the α5 subunit for the preparation of a medicament in the treatment of cognitive impairments in subjects suffering from Down syndrome. The application further relates to pharmaceutical compositions for treating cognitive impairments in subjects suffering from Down syndrome comprising a compound having inverse agonist functional selectivity for $GABA_A$ receptors containing the α5 subunit, or suitable pharmaceutically acceptable salt thereof, a surfactant (surface-active agent or tension-active agent), such as polyethoxylated castor oil and dimethyl sulfoxide (DMSO).

The present application also describes methods for enhancing cognitive function, or treating or lessening the severity of cognitive impairments, in subjects suffering from Down syndrome by administering to a subject in need thereof a pharmaceutically effective amount of one or more compounds having inverse agonist functional selectivity for $GABA_A$ receptors containing the α5 subunit. More particularly, the present application is concerned with the treatment of cognitive impairments, such as impairment in memory, learning capacity or both, in subjects suffering from Down syndrome.

BACKGROUND OF THE INVENTION

Down syndrome, also known as Trisomy 21, is the first genetic cause of mental retardation in man. It is a genetic disorder caused by the presence of all or part of a third copy of chromosome 21, causing delays in the way a child develops, both mentally and physically. Most text books quote the incidence of Down syndrome to be between one in 700 to 800 live births.

In addition to various physical characteristics, Down syndrome is often, though not always, characterized by varying degrees of cognitive impairment-impairment in memory, learning capacity or both. While advances in teaching methods and a trend toward educational mainstreaming has led to an improvement in cognitive development in those who have Down syndrome, there remain constitutive impairments that cannot be fully addressed through pedagogic methodology alone.

In addition, people with Down syndrome are at increased risk for certain medical problems. Some of the problems commonly faced by people with Down syndrome include heart defects, thyroid, muscle, joint, vision and hearing problems. Other conditions seen less frequently in Down syndrome include leukemia, and seizures. A variety of different approaches are used to treat these medical conditions. For example, if a person with Down syndrome has a seizure disorder, they would benefit from taking anti-seizure medications. People with thyroid problems often take thyroid replacement hormones. While these medications help with their medical condition, they do not cure Down syndrome.

Attempts at elaborating drugs for enhancing cognitive function in Down syndrome patients have been made. For example, piracetam is widely used as a purported means of improving cognitive function in children with Down syndrome. However, there have been reports undermining the proposition that piracetam may be effective in improving cognitive function in children with Down syndrome. (Lobaugh N J et al. Piracetam does not enhance cognitive abilities in moderate to high-functioning 7 to 13 year-old children with Down syndrome. Presented at the PAS/SPR meeting in San Francisco May 3, 1999; published in Archives of Ped and Adol Med, April 2001, 155(4):442-448 [ref 4]). In that study, neither cognitive nor behavioural measures demonstrated improvement under piracetam, even at doses associated with adverse effects.

Like Down syndrome patients, Ts65Dn mice, a murine model of Down syndrome carrying a segmental duplication of part of mouse chromosome 16, orthologous to most of the long arm of human chromosome 21, demonstrate learning and memory deficits, which are hypothetically due to selective decreases in the number of excitatory synapses in the brain rather than gross abnormalities in neuroanatomy. Theoretically, triplicate genes found in the Ts65Dn mice shift the optimal balance of excitation and inhibition in the dentate gyms (and other parts of the brain, perhaps) to a state in which excessive inhibition obscures otherwise normal learning and memory Reeves et al., Nature Genetics, 11(2):177-84 (1995) [ref 1].

It has recently been shown that use of $GABA_A$ antagonists in Ts65Dn mice increases memory, learning and neuronal plasticity (as assessed by long-term potentiation (LTP) protocols (Kleschevnikov et al., The Journal of Neuroscience, 24(37):8153-8160 (2004); [ref 2]). More recently, it has been shown that use of $GABA_A$ antagonists in a murine model of Down syndrome (Ts65Dn mice) normalized memory and declarative learning deficits as compared to euploid mice. (F. Fernandez et al., "Pharmacotherapy for cognitive impairment in a mouse model of Down syndrome," Nature Neuroscience, Advance Online Publication, (Feb. 25, 2007; [ref 3]).

These studies suggested the potential application of $GABA_A$ antagonist for restoring learning and memory performances in Down syndrome subjects.

Unfortunately, many $GABA_A$ antagonists tend to cause seizure in animal models as well as humans, making it clear that they cannot be used as cognition enhancing agents in subjects.

There is a large unmet medical need for the treatment of cognitive impairments associated with Down syndrome. Despite continued work, no notable medical treatments for mental retardation associated with Down syndrome have been forthcoming. Currently, medicines are not used to treat Down syndrome, rather medicines are used to treat other diseases associated with Down syndrome and other health conditions that may develop, such as antibiotics for ear infections and thyroid hormones for an underactive thyroid gland (hypothyroidism).

Thus, there is a need for a non-seizure inducing therapeutic treatment of cognitive impairments, such as impairment in memory, learning capacity or both, in subjects suffering from Down syndrome. The present invention meets this need and provides related advantages as well.

SUMMARY OF THE INVENTION

The foregoing and further needs are met by embodiments of the present invention, which provide a method for treating or lessening the severity of cognitive impairments in a subject suffering from Down syndrome, comprising administering to a subject in need thereof an effective amount of a compound having inverse agonist functional selectivity for $GABA_A$ receptors containing the α5 subunit, or an effective amount of a pharmaceutical composition comprising the compound, or pharmaceutically acceptable salt or prodrug thereof.

The foregoing and further needs are met by embodiments of the invention, which provide a method for enhancing cognitive function in a subject suffering from Down syndrome, comprising administering to a subject in need thereof a cognitive function enhancing amount of a compound having inverse agonist functional selectivity for $GABA_A$ receptors containing the α5 subunit, or a cognitive function enhancing effective amount of a pharmaceutical composition comprising the compound, or pharmaceutically acceptable salt or prodrug thereof.

The foregoing and further needs are additionally met by embodiments of the invention, which provide a pharmaceutical composition for treating or lessening the severity of cognitive impairments in subjects suffering from Down syndrome comprising an effective amount of a compound having inverse agonist functional selectivity for $GABA_A$ receptors containing the α5 subunit, or pharmaceutically acceptable salt or prodrug thereof, in combination with a surfactant (surface-active agent or tension-active agent), such as polyethoxylated castor oil, as excipient and dimethyl sulfoxide as co-solvent.

Additional characteristics and advantages of the invention will be recognized upon consideration of the following description and the appended claims.

BRIEF DESCRIPTION OF THE DRAWING

A better understanding of the features and advantages of the present invention will be obtained by reference to the following detailed description that sets forth illustrative embodiments, in which the principles of the invention are utilized, and the accompanying drawings:

FIG. 5A: Schematic representation of the DMTP protocol. Each day, mice underwent 1 acquisition trial and 3 retention trials (inter-trial interval was 60 sec). The position of the platform was changed every day, but remained constant within each session.

FIG. 5B: Performance (distance to platform; mean±SEM) of the mice between acquisition and retention trials. Data have been pooled on the seven training days. All mice showed a significant increase in behavioral accuracy within each session (p<0.0001). While placebo-treated mice and mice receiving 1 mg/kg of α5IA showed similar retention, mice that were treated with the 5 mg/kg dose of α5IA displayed a significantly higher performance (*p<0.05).

In placebo condition, Ts65Dn mice showed a trend for hypoanxiety (increased time in open arms) in comparison to euploid mice. Acute treatment with α5IA (one single 15 mg/kg i.p. injection; left part of the figure) did not modify the behavior of euploid mice, but significantly reduced the time spent in open arms by Ts65Dn mice (p<0.05). Under drug condition, Ts65Dn mice spent even less time in open arms than placebo-treated mice (p<0.025), which might be the indication of mild anxiogenic effects of α5IA in this genotype. However, these effects could also be attributed to a normalization of behavior in the Ts65Dn mice that "naturally" display some hypoanxiety traits.

Semi-chronic injections of α5IA in euploid mice (5 mg/kg 5 times a week for 2 weeks; right part of the figure) did not alter the anxiety levels (p>0.73).

Horizontal dotted line indicates the baseline performance of mice acutely treated with placebo. *p<0.05 ns: non-significant.

The study showed that α5IA did not induce anxiety-related behaviors.

Figure 7:
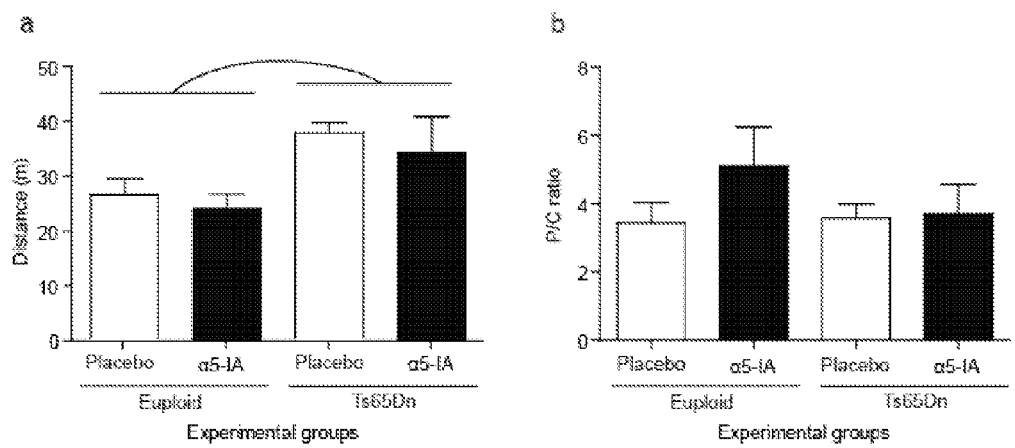

FIG. 7 depicts results from a locomotor activity and anxiety study of α5IA in Ts65Dn and euploid mice in the open field. Effects of α5IA (5 mg/kg) were evaluated on locomotion and anxiety in the open field.

FIG. 7A: Analysis of horizontal activity (traveled distances; mean±SEM) did not indicate any effect of treatment (F<1), underscoring that a single α5IA injection did not modify the gross locomotor activity in both euploid and Ts65Dn mice. Additionally, there was a significant effect of genotype (* p<0.025) that can be attributed to an overall hyperactivity of Ts65Dn mice as compared to euploid littermates and observed in all treatment conditions.

FIG. 7B: To assess anxiety during the open field session, a periphery-to-center exploration ratio was measured (P/C ratio; mean±SEM). Analysis on this value did not reveal any effects of genotype or treatment factors (Fs<1).

The study showed that α5IA did not alter locomotor activity and anxiety of Ts65Dn and euploid mice in the open field.

Figure 8:
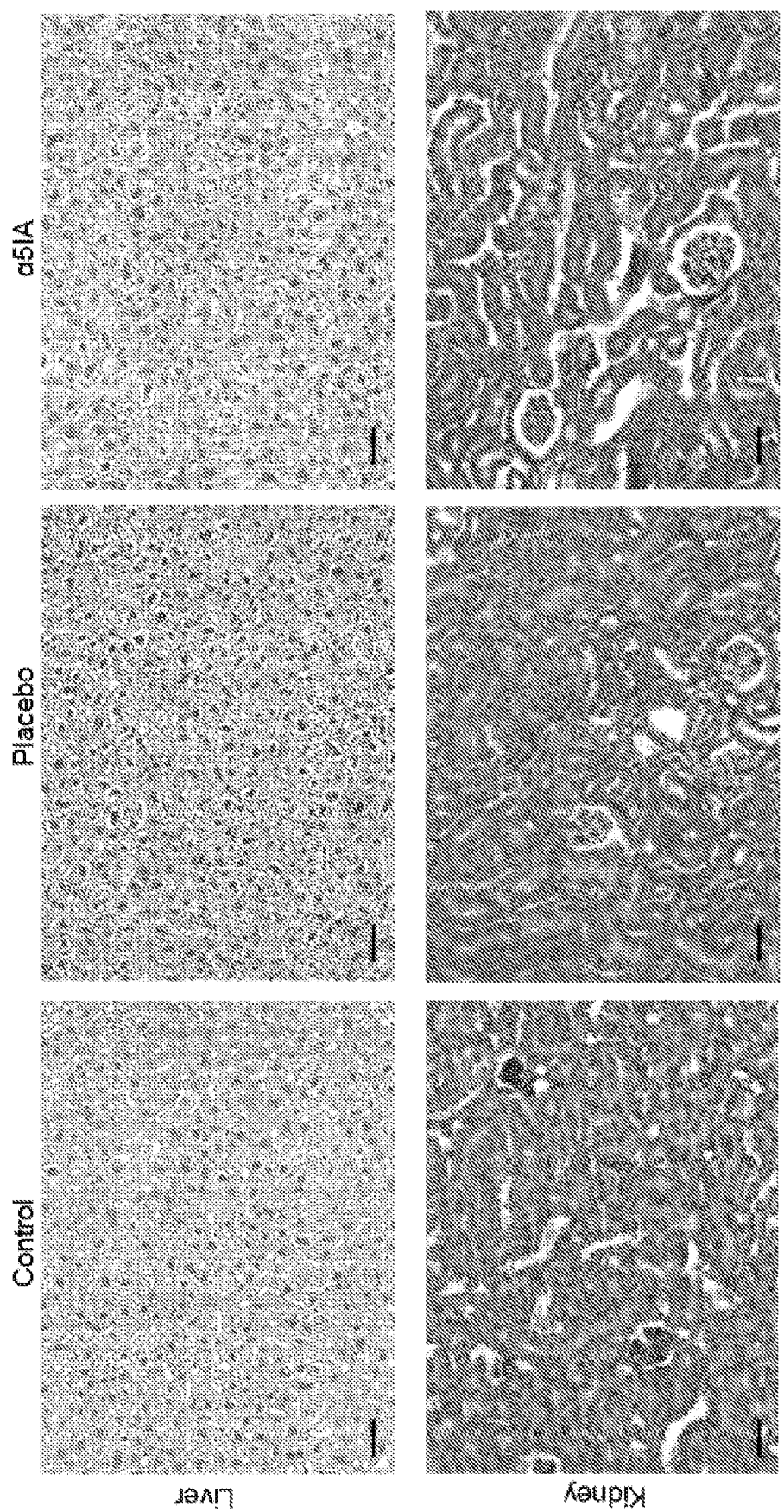

FIG. 8 depicts results from a histological lesion study of α5IA after chronic treatment. Following chronic treatment with α5IA (5 mg/kg; 5 injections/week for 5 weeks), different organs were ablated and processed for routine histopathological examination. As illustrated, hematein-eosin stainings did not reveal any significant macroscopic or microscopic tissue alterations in liver or kidney in any of the 3 experimental groups (non-injected, placebo-injected or α5IA treated mice). The same negative findings were observed following Periodic acid-Schiff staining of the tissues (not illustrated). Examination of brain, hepatic and renal tissues under polarized light revealed the lack of abnormal crystals in mice receiving injections of α5IA. The size and distribution of urine crystals (not illustrated) appeared to be very similar in the different groups. The scale bar represents 100 μm. The study showed that α5IA did not induce any histological lesions after chronic treatment.

Figure 9:
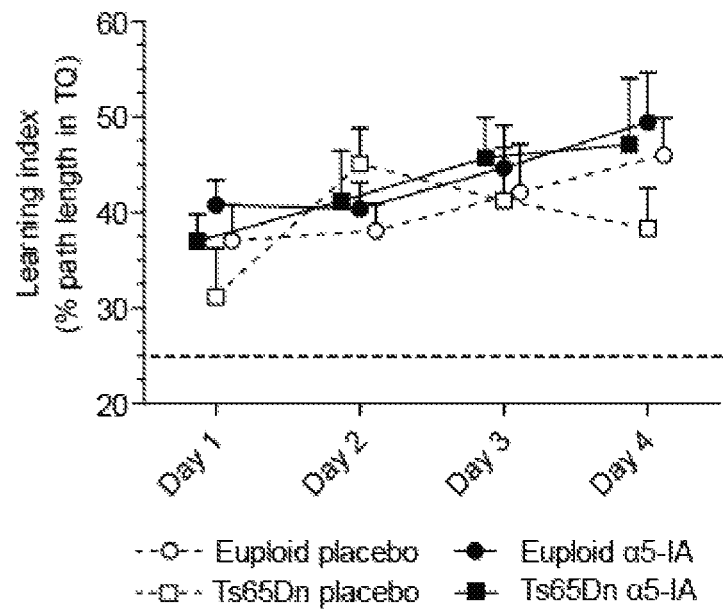

FIG. 9 depicts results from a spatial impairment study in Ts65Dn mice. Following evaluation of spatial memory in the Morris water maze, mice were trained during 4 days in a visually-guided navigation task (cued visible platform). Performance was assessed using an unbiased learning index (same as in FIG. 11). Analysis indicated that behavioral accuracy to locate the visible platform slightly increased with each session ($p<0.03$) with no effect of genotype ($p>0.55$) or treatment ($p>0.16$). The horizontal dotted line at 25% represents level of performance due to random navigation in the pool. As illustrated, all trained groups performed largely above this level. The study showed that spatial impairments in Ts65Dn mice were not due to visual deficits.

Figure 10:
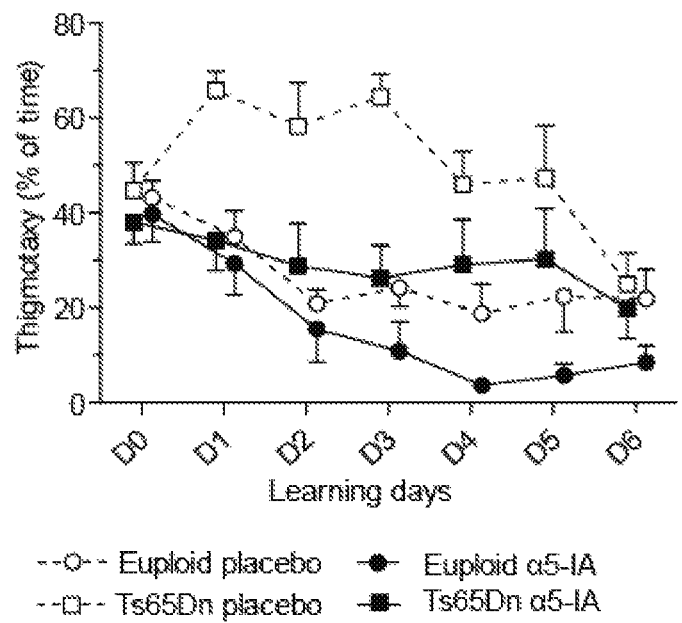

FIG. 10 depicts results from a Morris water maze study. A robust effect of α5IA was observed on thigmotaxy ("wall-seeking behavior"). This inadequate strategy to locate the platform in the water maze was strongly decreased in mice following treatment with α5IA, particularly in Ts65Dn mice ($p<0.001$). Follow-up analysis indicated that Ts65Dn mice were more thigmotactic than control mice ($p<0.0001$). This effect was observed under placebo ($p<0.00025$) and, to a lesser extent, after treatment with α5IA ($p<0.05$). The study showed that α5IA relieved the use of irrelevant behavioral navigating strategies in the Morris water maze.

Figure 11:
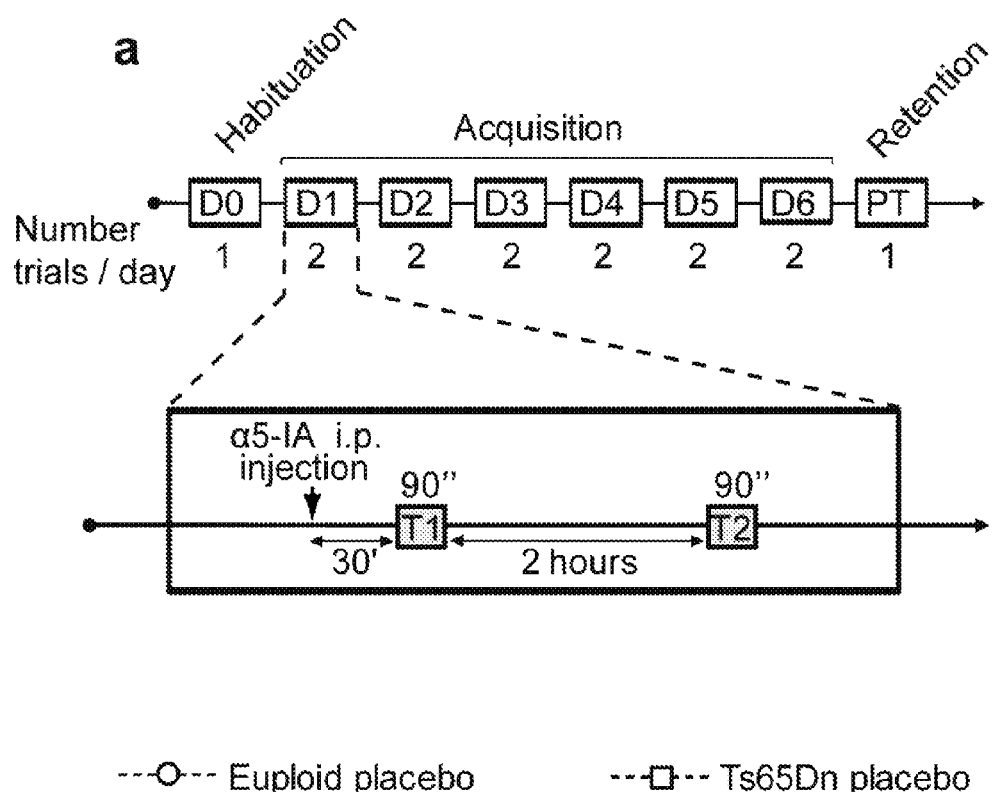
Figure 11:
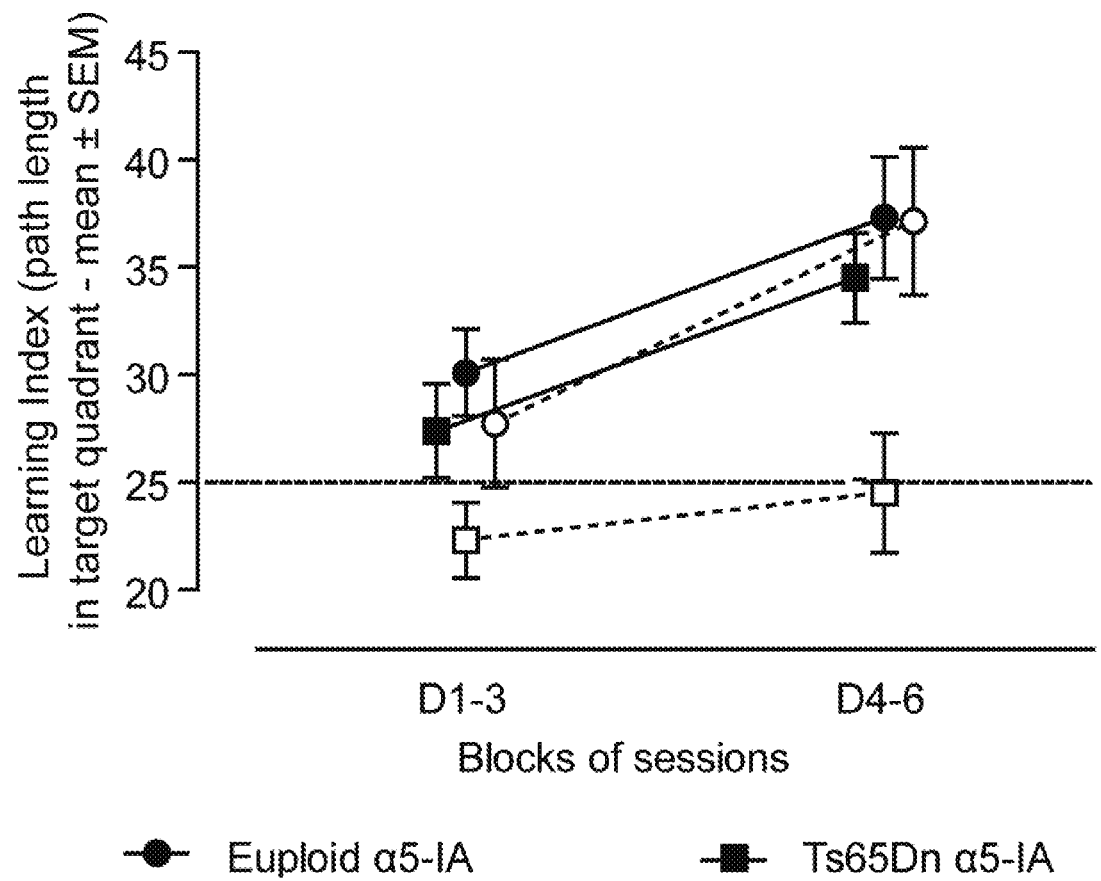
Figure 11:
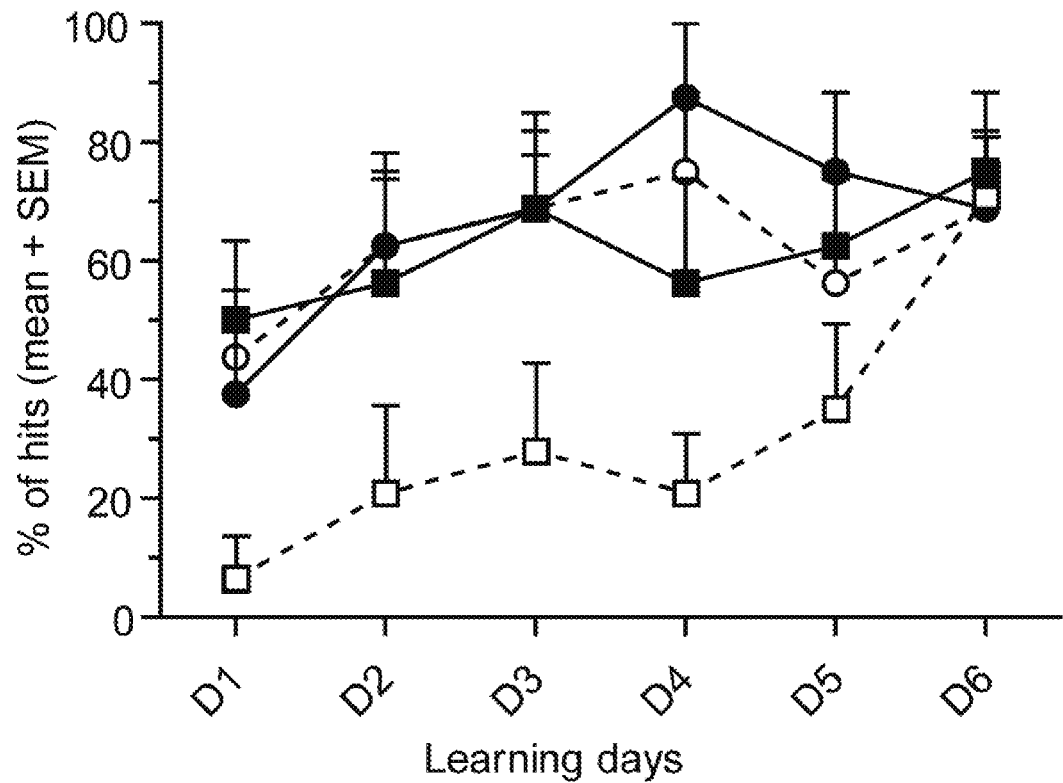
Figure 11:
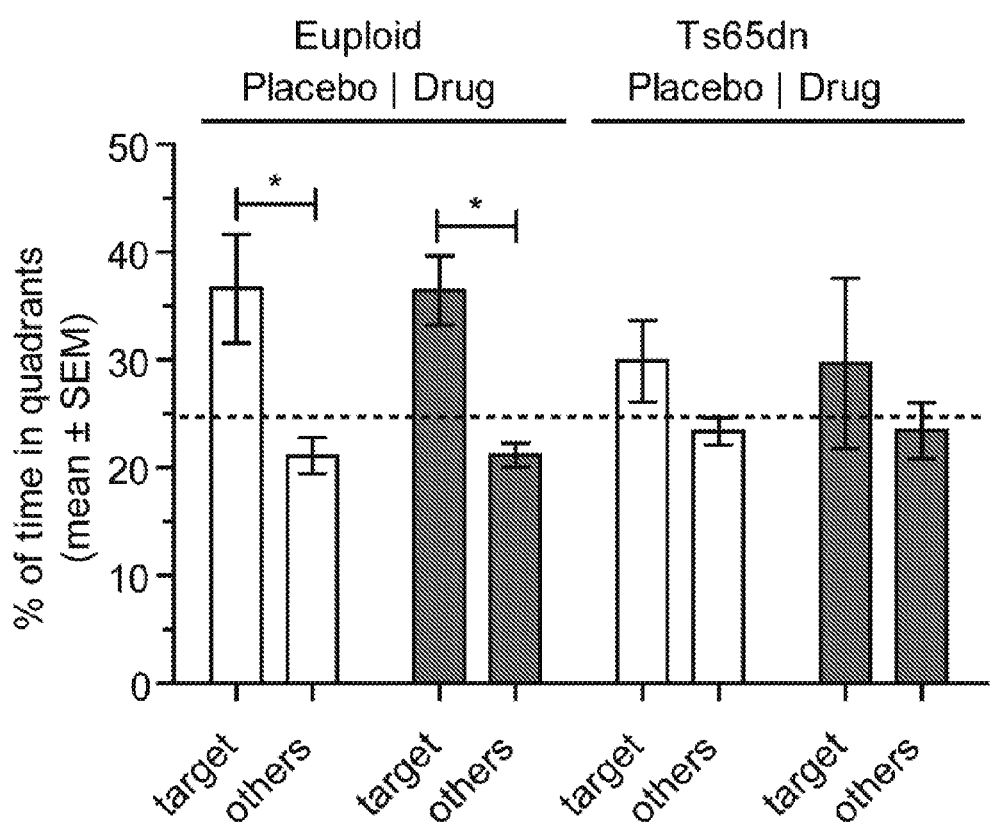

FIG. 11 depicts results from a spatial learning study in Ts65Dn mice. The study shows that α5IA restored spatial learning study in Ts65Dn mice.

FIG. 11A: Mice learnt to navigate in a water tank to reach an invisible platform (D1-6). Spatial memory was assessed using a probe trial test (PT).

FIG. 11B: Data on learning performance have been pooled in two blocks of three days. Ts65Dn mice demonstrated decreased learning index ($p<0.0025$) that was corrected by treatment with α5IA.

FIG. 11C: A hit was defined as reaching the platform before 90 sec. Ts65Dn mice showed a deficit ($p<0.025$) that was reversed after treatment with α5-IA.

FIG. 11D: Only euploid mice showed a spatial bias for the platform target quadrant during probe trial ($p<0.05$). See Exemplification for comments.

For FIGS. 11B and 11D, horizontal dotted lines at 25% correspond to random performance. (* $P<0.05$, n=8 for each group)

FIG. 12 depicts results from a neuronal activity and recognition memory deficit study in Ts65Dn mice. The study showed that α5IA potentiated neuronal activity and alleviated recognition memory deficits in Ts65Dn mice.

Figure 12A:
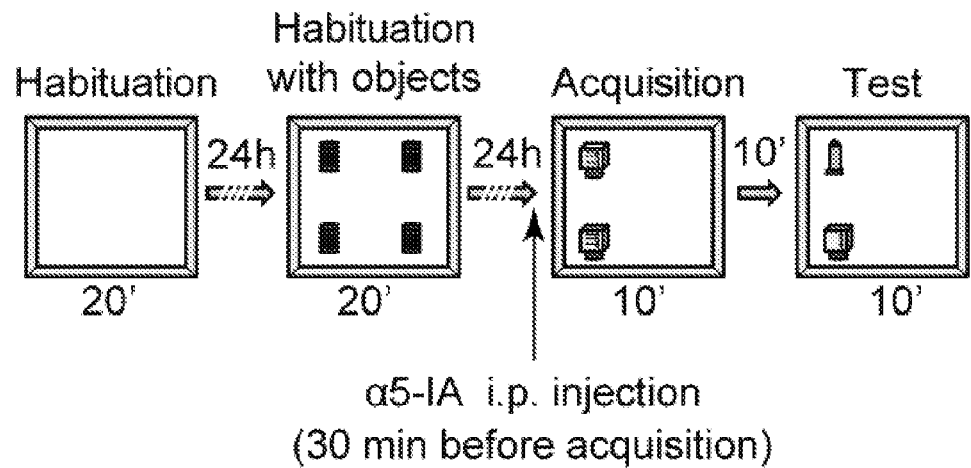
Figure 12A:
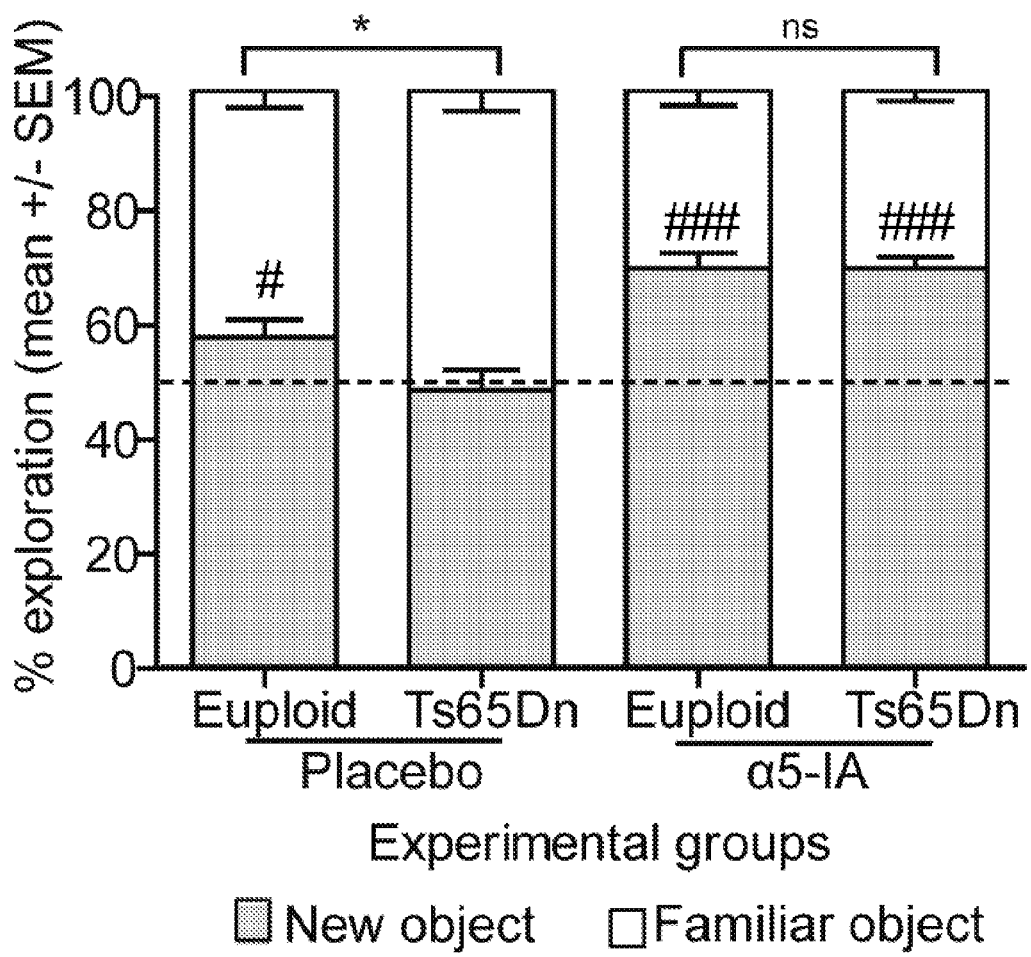

FIG. 12A: When trained in the object recognition task Ts65Dn mice showed impaired memory. Following i.p. injection of α5IA (5 mg/kg), both euploid and Ts65Dn mice largely improved their recognition performance and the deficit of Ts65Dn mice was abolished. * Difference between groups ($p<0.05$, n=8 for each group; ns: non-significant;) # Performance above the 50% random score (#: $p<0.05$; ###: $p<0.001$)

Figure 12B:
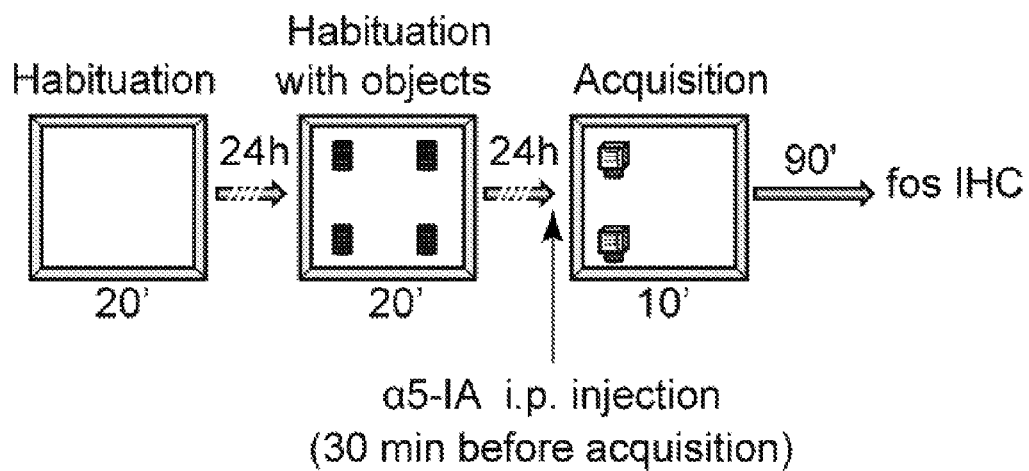
Figure 12B:
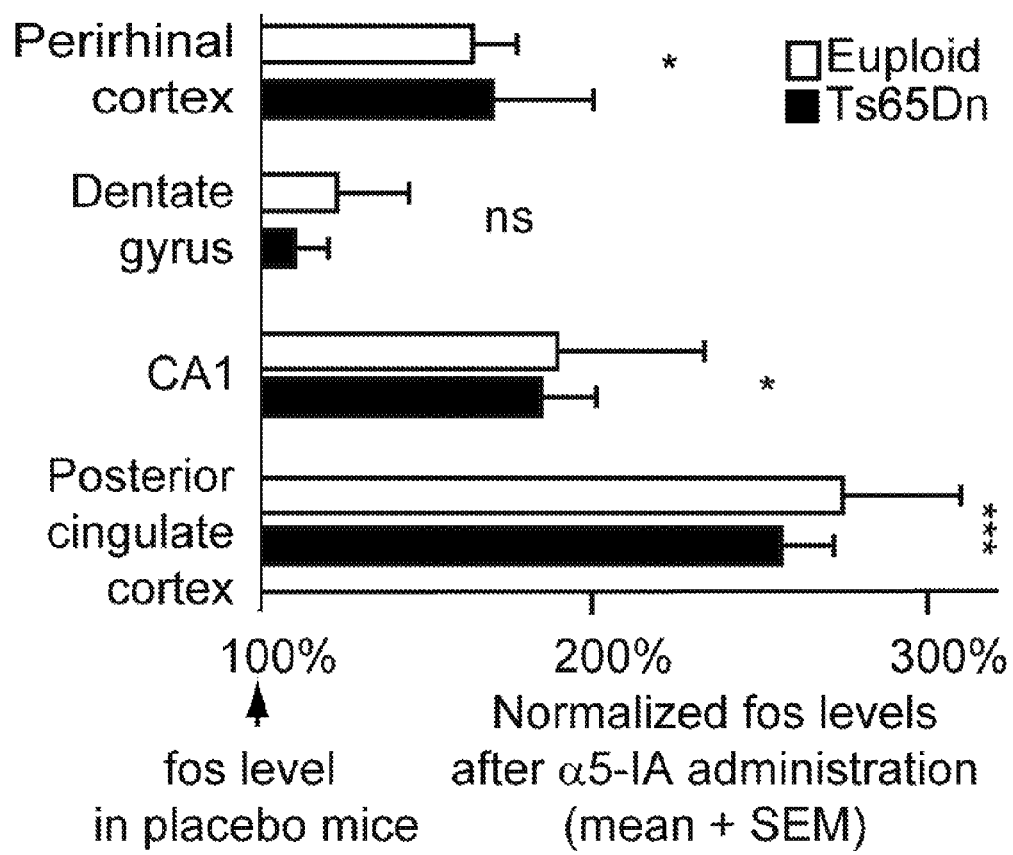

FIG. 12B: Following acquisition in the object recognition task, mice were sacrificed and their brains processed for quantitative immunohistochemical assessment of fos protein. Histograms depict the relative increase of fos immunoreactivity in α5IA treated mice normalized against values obtained for their placebo-treated littermates. In all brain regions sampled, except the dentate gyrus, a significant increase of fos was observed after α5IA injection (*: $p<0.05$; ***: $p<0.001$, n=3-5 for each group).

Figure 13:
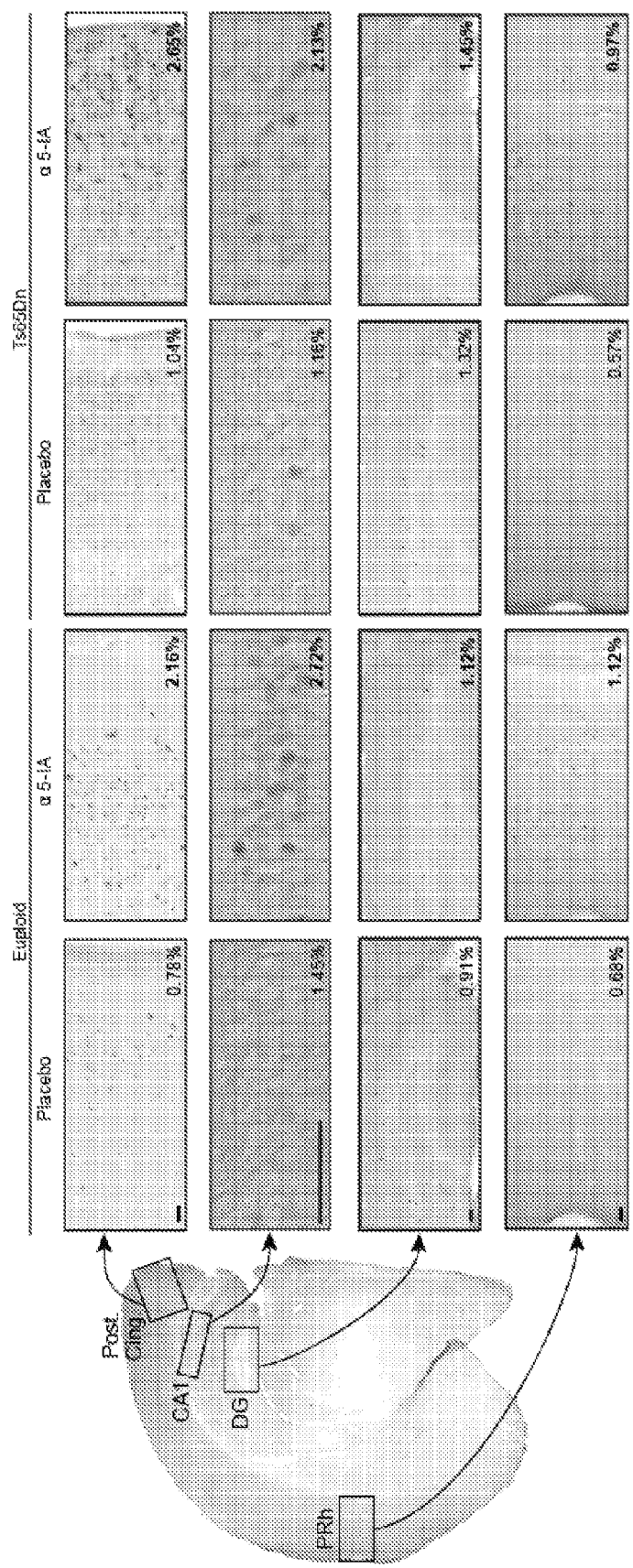

FIG. 13 depicts results from a neuronal activity study of α5IA during a novel object recognition task. The study showed an increase of neuronal activity by α5IA during the novel object recognition task. Representative photomicrographs of the brain regions of interest (depicted on the left hemibrain microphotograph: posterior cingulate cortex (Post.Cing.), CA1 field (CA1), dentate gyrus (DG) and perirhinal cortex (PRh)) immunostained against fos protein in the different experimental groups (Scale bar=100 μm). Note the overall increase of fos immunoreactivity following α5IA treatment in all regions of interest, except the dentate gyrus. This Figure is complementary to FIG. 12B.

FIG. 14 summarizes the results obtained in the study of FIG. 13. Statistical analysis confirms the qualitative observations illustrated in FIG. 13, namely an increase of neuronal activity by α5IA in control and Ts65Dn mice, in the perirhinal cortex and posterior cingulate cortex, as well as in the hippocampus, in particular the CA1 field. Only the activity in the dentate gyrus is not significantly affected by the treatment.

DEFINITIONS

Unless defined otherwise, all technical and scientific terms used herein have the same meaning as is commonly understood by one of skill in the art to which this invention belongs. All patents and publications referred to herein are incorporated by reference.

The definitions set forth in this application are intended to clarify terms used throughout this application. The term "herein" means the entire application.

As used herein, an "effective amount" of a compound or pharmaceutically acceptable composition is an amount of the active pharmaceutical ingredient that provides temporary relief of one or more impairments of cognition in subjects suffering from Down syndrome. Thus an effective amount of an active pharmaceutical ingredient is expected to provide relief of impaired memory, impaired learning capacity or both. Although the relief provided is considered temporary, the person skilled in the art will recognize that even a temporary improvement in learning capacity can have a long term beneficial effect on long-term learning, as learning tends to be cumulative over time. Thus, the use of the qualifier "temporary" is not intended to exclude potential long-term improvements in cumulative learning. Such amount may be administered as a single dosage or may be administered according to a regimen, whereby it is effective.

As used herein, "treatment" means any manner in which the symptoms or pathology of a condition, disorder or disease are ameliorated or otherwise beneficially altered.

As used herein, "biological activity" refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, "pharmaceutical activity" refers to the activity of the compounds herein to treat or lessen the severity of cognitive impairments in subjects suffering from Down syndrome.

The term "agonist" is defined as a compound that increases the activity of a receptor when it contacts the receptor.

The term "antagonist" is defined as a compound that competes with an agonist or inverse agonist for binding to a receptor, thereby inhibiting or blocking the action of an agonist or inverse agonist on the receptor. However, an antagonist (also known as a "neutral" antagonist) has no effect on constitutive receptor activity.

The term "inverse agonist" refers to an agent which binds to the same receptor binding-site as an agonist for that receptor and reverses constitutive activity of receptors. Inverse agonists exert the opposite pharmacological effect of a receptor agonist. Inverse agonists are effective against certain types of receptors (e.g. certain GABA receptors) which have intrinsic activity without the action of a ligand upon them (also referred to as 'constitutive activity'.) Receptor agonists, antagonists and inverse agonists bind to the same receptor types. The pharmacological effect of an inverse agonist is measured as the negative value of the agonist primarily due to the historical findings of the already known agonist. Therefore, if the agonist has a positive value and the inverse agonist has a negative value, the antagonist for the receptor takes both the agonist and inverse agonist back to a neutral state.

The term "subject" refers to an animal, for example a mammal, such as a human, who is the object of treatment, observation or experiment.

The term "selective" is defined as a property of a compound whereby an amount of the compound sufficient to effect a desired response from a particular receptor type, subtype, class or subclass causes a substantially smaller or no effect upon the activity of other receptor types.

As used herein, $EC_{50}$ refers to a dosage, concentration or amount of a particular test compound that elicits a dose-dependent response at 50% of maximal expression of a particular response that is induced, provoked or potentiated by the particular test compound.

The $EC_{50}$ for an agonist is intended to denote the concentration of a compound needed to achieve 50% of a maximal response seen in an in vitro assay. For inverse agonists, $EC_{50}$ is intended to denote the concentration of a compound needed to achieve 50% inhibition of a receptor response from basal, no compound, levels.

As used herein, the term "coadministration" of pharmacologically active compounds refers to the delivery of two or more separate chemical entities, whether in vitro or in vivo. Coadministration refers to the simultaneous delivery of separate agents; to the simultaneous delivery of a mixture of agents; as well as to the delivery of one agent followed by delivery of a second agent or additional agents. In all cases, agents that are coadministered are intended to work in conjunction with each other.

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof (i.e., also include counterions). Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, phosphoric, and the like; and the salts prepared from organic acids such as lactic, maleic, citric, benzoic, methanesulfonic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; nonaqueous media like ether, ethyl acetate, ethanol, isopropanol, or acetonitrile can be used.

The term "salt" means pharmaceutically acceptable acid addition salts obtainable by treating the base form of a functional group, such as an amine, with appropriate acids such as inorganic acids, for example hydrohalic acids; typically hydrochloric, hydrobromic, hydrofluoric, or hydroiodic acid; sulfuric acid; nitric acid; phosphoric acid and the like; or organic acids, for example acetic, propionic, hydroacetic, 2-hydroxypropanoic acid, 2-oxopropanoic acid, ethandioic, propanedioic, butanedioic, (Z)-2-butenedioic, (E)-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic acid, cyclohexanesulfamic, 2-hydroxybenzoic, 4-amino-2-hydroxybenzoic, and other acids known to the skilled practitioner.

As used herein, the phrase "active pharmaceutical ingredient" (or alternatively "active pharmaceutical agent") is intended to mean a compound or combination of compounds, at least one of such compounds is a compound having inverse agonist functional selectivity for $GABA_A$ receptors containing the α5 subunit as described in more detail herein. Thus, unless otherwise limited (e.g. by the delimiters "consisting of or "consisting essentially of") recitation of an active pharmaceutical ingredient requires the presence of at least one compound having inverse agonist functional selectivity for $GABA_A$ receptors containing the α5 subunit, but may also include one or more additional pharmaceutical compounds that do not detract from, and in some cases may enhance, the activity of the $GABA_A$ α5 subtype receptor functionally selective inverse agonist.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs.

As used herein, a prodrug is a compound that, upon in vivo administration, is metabolized or otherwise converted to the biologically, pharmaceutically or therapeutically active form of the compound. In other words, a pro-drug is a derivative of a compound, usually with significantly reduced pharmacological activity, which contains an additional moiety that is susceptible to removal in vivo yielding the parent molecule as the pharmacologically active species. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, once a pharmaceutically active compound is identified, those of skill in the pharmaceutical art generally can design prodrugs of the compound [see, es., Nogrady (1985) Medicinal Chemistry A Biochemical Aprroach, Oxford University Press, New York, pages 388-392].

An example of a pro-drug is an ester which is cleaved in vivo to yield a compound of interest. Such esters may be formed by esterification, for example, of any of the carboxylic acid groups (—C(═O)OH) in the parent compound, with, where appropriate, prior protection of any other reactive groups present in the parent compound, followed by deprotection if required.

Examples of such metabolically labile esters include those of the formula —C(═O)OR wherein R is: $C_{1-7}$alkyl (e.g., Me, Et, -nPr, -iPr, -nBu, -sBu, -iBu, tBu); $C_{1-7}$-aminoalkyl (e.g., aminoethyl; 2-(N,N-diethylamino)ethyl; 2(4-morpholino)ethyl); and acyloxy-$C_{1-7}$alkyl (e.g., acyloxymethyl; acyloxyethyl; pivaloyloxymethyl; acetoxymethyl; 1 acetoxyethyl; 1-(1-methoxy-1-methyl)ethyl-carbonyloxyethyl; 1-(benzoyloxy)ethyl; isopropoxy-carbonyloxymethyl; 1-isopropoxy-carbonyloxyethyl; cyclohexyl-carbonyloxymethyl; 1 cyclohexyl-carbonyloxyethyl; cyclohexyloxy-carbonyloxymethyl; 1-cyclohexyloxy-carbonyloxyethyl; (4-tetrahydropyranyloxy)carbonyloxymethyl; 1-(4-tetrahydropyranyloxy)carbonyloxyethyl; (4-tetrahydropyranyl) carbonyloxymethyl; and 1 (4-tetrahydropyranyl) carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Pro-drugs of a variety of compounds, and materials and methods for derivatizing the parent compounds to create the pro-drugs, are known and may be adapted to the present invention.

Other derivatives include coupling partners of the compounds in which the compounds is linked to a coupling partner, e.g. by being chemically coupled to the compound or physically associated with it. Examples of coupling partners include a label or reporter molecule, a supporting substrate, a carrier or transport molecule, an effector, a drug, an antibody or an inhibitor. Coupling partners can be covalently linked to compounds of the invention via an appropriate functional group on the compound such as a hydroxyl group, a carboxyl group or an amino group. Other derivatives include formulating the compounds with liposomes.

Certain exemplary pharmaceutical compositions and pharmaceutically acceptable derivatives will be discussed in more detail herein below.

DETAILED DESCRIPTION CERTAIN PREFERRED EMBODIMENTS OF THE INVENTION $GABA_A$ receptors are ligand-gated ion channels that are the major modulators of the inhibitory tone throughout the central nervous system (CNS). They are the site of action of a number of clinically important drugs, including benzodiazepines (BZs), barbiturates, and anesthetics. $GABA_A$ receptors exist as a number of subtypes formed by the co-assembly of gene family subunit polypeptides, the majority of which contain $\alpha$, $\beta$ and $\gamma$ subunits. Each receptor subtype has a distinct pattern of expression within the mammalian brain, suggesting a defined physiological role.

The binding of GABA to its receptor can be modulated by simultaneous binding of chemical compounds to allosteric sites on the ion channel complex, the most studied of which is the BZ binding site. Based on their modulatory effects on GABA-induced $GABA_A$ receptor activation, BZ site ligands are classified into either agonists (positive allosteric modulators), inverse agonists (negative allosteric modulators) or antagonists.

BZ agonists exert their effect by increasing the frequency of channel opening in the presence of GABA resulting in an increase in chloride flux through the ion channel to give a net hyperpolarization of the neuron and a decreased excitability. Conversely, BZ inverse agonists decrease the frequency of channel opening of GABA and thereby increase neuronal excitability. Antogonists do not have an effect per se on GABAergic activity. However, they inhibit the effects of agonists by competition.

As discussed previously, $GABA_A$ receptor antagonists have been demonstrated to increase memory and declarative learning in a murine model of Down syndrome (Ts65Dn mice) [ref 5]. However, many $GABA_A$ antagonists tend to cause seizure in animal models as well as humans, thereby preventing their use as cognition enhancing agents in subjects.

In the related field of cognition enhancement in subjects suffering from Alzheimer's disease and other forms of dementias, research efforts have turned to $GABA_A$ inverse agonists. For example, it has been reported that the benzodiazepine receptor inverse agonist β-CCM enhanced spatial learning in the Morris watermaze (McNamara and Skelton, Psychobiology, 21(2):101-108 (2002) [ref 5]; See also Venault et al., Nature, 321(6073):864-866 (1986) [ref 14]). However, β-CCM and many conventional benzodiazepine receptor inverse agonists are proconvulsant or convulsant which makes it clear that they cannot be used as cognition enhancing agents in humans.

It has been reported that a certain category of $GABA_A$ inverse agonists have cognitive enhancement properties, without the undesired proconvulsant or convulsant effects. Thus, functionally selective inverse agonists at the benzodiazepine site of $GABA_A$ α5 receptors have been found to enhance cognition in rats and/or monkeys without anxiogenic and proconvulsant side effects. (See for example, Ballard et al., Psychopharmacology, 202:207-223 (2009) [ref 6]; Atack et al., Neuropharmacology, 51:1023-1029 (2006) [ref 7]).

For example, the triazolophthalazine α5IA has been reported to bind with equal affinity to the benzodiazepine binding site of $GABA_A$ receptors containing either an α1, α2, α3 or α5 subunit (Sternfeld et al., J. Med. Chem., 47:2176-2179 (2004) [ref 8]; Dawson et al., The Journal of Pharmacology and Experimental Therapeutics, 316(3):1335-1345 (2006) [ref 9]).

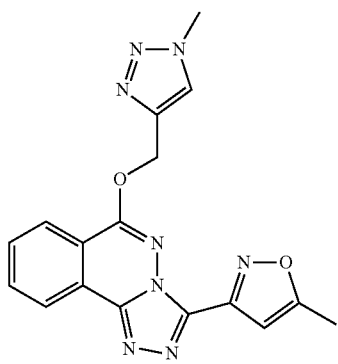

IAα5

Although α5IA is non-selective in terms of binding affinity, it has inverse agonist efficacy selective for the α5 subtype in that it exhibits inverse agonism at this subtype but has low or antagonist efficacy at the α1, α2 and α3 subtypes (Dawson et al. [ref 9]). Consequently, the in vitro and in vivo effects of this compound are exerted primarily via $GABA_A$ receptors containing the α5 subunit (Dawson et al. [ref 9]). More specifically, α5IA has been shown to enhance long-term potentiation in a mouse hippocampal slice assay (a putative model for synaptic remodeling associated with learning and memory) and to enhance cognitive performance in variant of the Morris water maze task (Dawson et al. [ref 9]).

Recently, this same compound has been shown to decrease the cognition-impairing effects of ethanol in healthy normal volunteers (Nutt et al., Neuropharmacology, 53:810-820 (2007) [ref 10]).

Other functionally selective inverse agonists at the benzodiazepine site of $GABA_A$ α5 receptors have been reported (ref 6 & 7).

This type of compound has been suggested to find use in treating cognitive impairments associated with Alzheimer's disease. However, there is a question as to whether this type of compounds might actually find use in such treatment.

Indeed for Alzheimer disease recent publications show that disinhibited neurons will degenerate while less excited (relatively over-inhibited) neurones will survive. (Schmitt 2005 <<Neuro-modulation, aminergic neuro-disinhibition and neuro-degeneration. Draft of a comprehensive theory for Alzheimer disease>> Med Hypotheses. 2005; 65(6):1106-19. Epub 2005 Aug. 24 [ref 15]). In mouse models of Alzheimer's disease there is an aberrant increase in network excitability and compensatory inhibitory mechanisms in the hippocampus (Palop et al. <<Aberrant excitatory neuronal activity and compensatory remodeling of inhibitory hippocampal circuits in mouse models of Alzheimer's disease." Neuron. 2007 Sep. 6; 55(5):697-711 [ref 16]). Thus the use of α5I1A might not be the best cure for Alzheimer's disease. However, the efficacy of functionally selective inverse agonists at the benzodiazepine site of $GABA_A$ α5 receptors in the enhancement of cognitive functioning, especially memory, learning, or both in subjects suffering from Dow syndrome has never been investigated nor reported.

The present investigators have, in part, focused their efforts on the development of molecules that enhance cognitive functioning, especially memory, learning, or both in subjects suffering from Down syndrome, without producing significant anxiogenic-like and/or convulsant or proconvulsant side effects.

It has now been discovered that compounds having inverse agonist functional selectivity for $GABA_A$ receptors containing the α5 subunit may possess superior efficacy at treating cognitive impairments associated with Down syndrome. Accordingly, the present investigators have demonstrated that inverse agonists that are selective for the α5 $GABA_A$ receptor can be used to provide a medicament which is useful for treating cognitive impairments in Down syndrome subjects. This unexpected finding is unprecedented and may lead to the development of an effective treatment of cognitive impairments associated with Down syndrome.

This is based on the present investigators' findings that treatment of Ts65Dn mice with the functionally selective α5 $GABA_A$ inverse agonist α5IA not only restores their mnesic deficit but also surprisingly enhances their performance to the level of that of wild-type mice also treated with α5IA. In a totally unexpected way, α5IA-treated Ts65Dn mice performed better in an object recognition task than wild-type mice that received a placebo. Without wishing to be bound to any particular theory, it is believed that the effect of α5IA in Ts65Dn mice is not a mere "normalization" of cognitive performance (i.e., return to normal levels), as observed in Ts65Dn mice treated with $GABA_A$ antagonists pentylenetetrazole (Fernandez et al. 2007), or a mere promnesic effect. In contrast, a synergic effect is observed that goes beyond the mere reversal of the pathologic state associated with excessive GABAergic transmission. These results, as reported in Examples 2 and 3, demonstrate that compounds having inverse agonist functional selectivity for $GABA_A$ receptors containing the α5 subunit may possess superior efficacy at treating cognitive impairments associated with Down syndrome, and can have dual/synergic therapeutic and promnesic effects. As such, they represent promising candidates for an effective treatment of cognitive impairments in subjects suffering from Down syndrome.

The observed performance enhancement could not be reasonably expected because the synapses in trisomic mice have more GABA. It could therefore be expected that inhibiting GABA activity would be more difficult in Ts65Dn mice. Inverse agonist α5IA exhibits two additional effects that could not be reasonably expected:

1) It restores mnesic deficits of Ts65Dn mice as compared to non treated mice (this was not predictable)
2) It also enhances the memory performance of Ts65Dn mice, such they become as performant as wild-type mice also treated with α5IA The work reported by Fernandez et al. [ref 3] with GABA antagonists (pentylenetetrazol) did not show a cognition enhancement effect in treated mice as compared to control non-treated mice.

Accordingly, in one aspect, the present invention provides methods and pharmaceutical formulations for treating or lessening the severity of cognitive impairments associated with Down syndrome, comprising administering to a subject suffering from Down syndrome an effective amount of a composition comprising a compound having inverse agonist functional selectivity for $GABA_A$ receptors containing the α5 subunit. Thus, the present invention provides compounds having inverse agonist functional selectivity for $GABA_A$ receptors containing the α5 subunit for use as a medicament in the treatment of cognitive impairments in subjects suffering from Down syndrome. The present invention also provides the use of compounds having inverse agonist functional selectivity for $GABA_A$ receptors containing the α5 subunit for the preparation of a medicament in the treatment of cognitive impairments in subjects suffering from Down syndrome.

In another aspect, the present invention provides methods and pharmaceutical formulations for enhancing cognitive function in a patient suffering from Down syndrome, comprising administering to the subject a cognitive function enhancing amount of a compound having inverse agonist functional selectivity for GABA$_A$ receptors containing the α5 subunit. Thus, the present invention provides compounds having inverse agonist functional selectivity for GABA$_A$ receptors containing the α5 subunit for use as a medicament for enhancing cognitive function in subjects suffering from Down syndrome. The present invention also provides the use of a compound having inverse agonist functional selectivity for GABA$_A$ receptors containing the α5 subunit for the preparation of a medicament for enhancing cognitive function in a patient suffering from Down syndrome.

Thus, the present invention seeks to improve cognitive functioning—e.g. memory and learning—in individuals whose cognitive functioning is impaired as a result of Down syndrome.

1. Compounds

Minimally, the compounds useful for carrying out the inventive method exhibit inverse agonist functional selectivity for GABA$_A$ receptors containing the α5 subunit, over the GABA$_A$ α1 α2 or α3 receptor subtypes.

In certain exemplary embodiments, the compounds also exhibit selective binding affinity for the GABA$_A$ α5 receptor subtype, over the GABA$_A$ α1 α2 or α3 receptor subtypes.

In certain exemplary embodiments, the compound has one of the following structures:

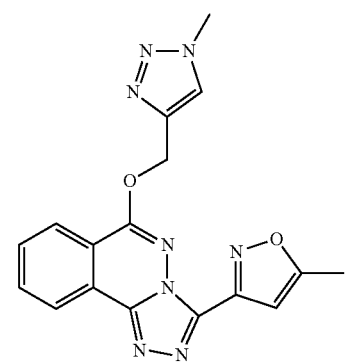

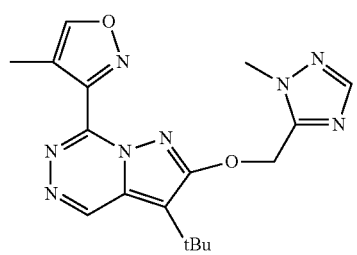

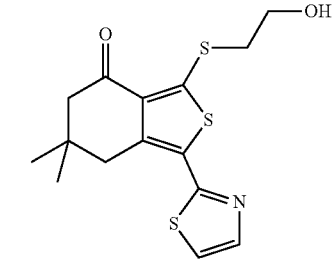

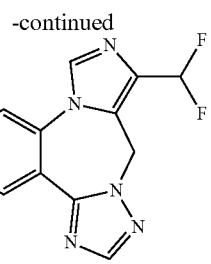

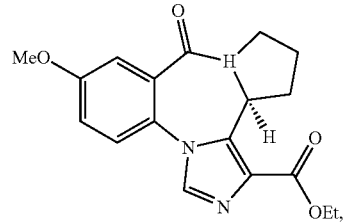

or pharmaceutically acceptable salt or prodrug thereof.

The above compounds have been shown to be functionally selective inverse agonists at the benzodiazepine site of GABA$_A$ α5 receptors, while lacking the unwanted side effects associated with inverse agonist activity at other GABA$_A$ receptor subtypes (i.e., anxiogenesis or convulsant or proconvulsant activity). (Steinfeld et al. 2004 [ref 8], Chambers et al. 2004 [ref 11] et Ballard et al. 2009 [ref 6], respectively). These compounds can be prepared by the methodologies described in the above-referenced publications.

In certain exemplary embodiments, the compound has one of the following structures:

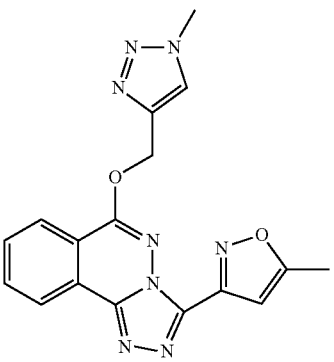

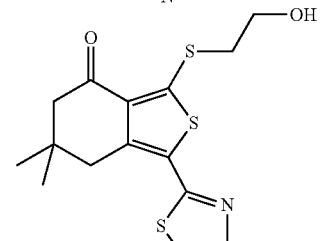

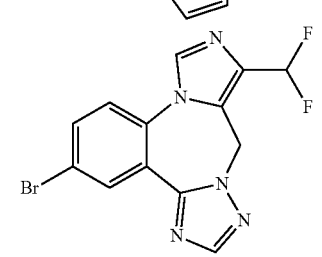

-continued

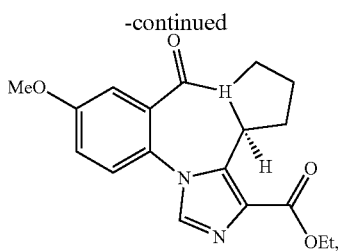

or pharmaceutically acceptable salt or prodrug thereof.

In certain exemplary embodiments, the compound has the following structure:

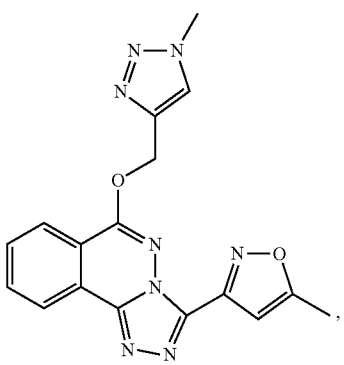 [SMILES: Cc1cc(-c2nnc3c4ccccc4c(OCc4cn(C)nn4)nn23)no1]

or pharmaceutically acceptable salt or prodrug thereof.

2. Identification of Preferred Compounds Using Assays that Identify Compounds that are Functionally Selective for the $GABA_A$ α5 Receptor Subtype Receptor Binding Affinity/Selectivity In certain embodiments, compounds useful for carrying out the inventive method have inverse agonist functional selectivity for $GABA_A$ receptors containing the α5 subunit. In certain preferred embodiments, the compounds are functionally selective for the α5 subunit as partial or full inverse agonists while substantially being antagonists at the α1, α2 and α3 subunits. In certain other embodiments, the compounds of the invention are binding selective for the α5 subunit relative to the α1, α2 and α3 subunits.

Particular compounds may be empirically selected for treating or lessening the severity of cognitive defects associated with Down syndrome using known in vitro or in vivo animal models.

For example, compounds can be evaluated for their affinity at $GABA_A$ receptor subtypes, in particular the α5 $GABA_A$ receptor subtype. The compounds may be assayed by measured competition for [$^3$H]flumazenil binding to cells expressing receptors of composition α1β3γ2, α2β3γ2, α3β3γ2 and α5β3γ2, such as those described in US 2006/0084642.

In certain embodiments, the compounds exhibit a Ki value for displacement of [$^3$H]flumazenil from α5 subunits of the rat $GABA_A$ receptor of 100 nM or less. In certain embodiments, the compounds exhibit a $Ki^{rat}_{α5}$ value≤75 nM, preferably ≤50 nM, preferably ≤25 nM, preferably ≤20 nM, preferably ≤10 nM, preferably ≤5 nM, more preferably ≤1 nM.

In certain embodiments, the compounds are selective for the $GABA_A$ α5 subtype receptor relative to the α1, α2 and α3 subtypes. This binding selectivity can also be assessed by measured competition for [$^3$H]flumazenil binding to cells expressing receptors of composition α1β3γ2, α2β3γ2, α3β3γ2 and α5β3γ2, such as those described in US 2006/0084642. In certain embodiments, the compound's binding affinity at the $GABA_A$ α5 receptor subtype is at least 2-fold greater, preferably 5-fold greater, more preferably 10-fold greater, more preferably 20-fold greater, more preferably 30-fold greater, more preferably 40-fold greater, more preferably 50-fold greater, still more preferably 60-fold greater than its binding affinity at the $GABA_A$ α1 α2 or α3 receptor subtypes. The binding affinity at the $GABA_A$ α5 receptor subtype may not be greater than the α1 α2 or α3 receptor subtypes by a similar amount. For example, the binding affinity at the $GABA_A$ α5 receptor subtype may be about 10 fold greater than the α3 receptor subtype, about 20 fold greater than the α2 receptor subtype, and about 60 fold greater than the α1 receptor subtype (See AIα5, Steinfeld et al. [ref 7]), Receptor Functional Selectivity In certain embodiments, compounds useful for carrying out the inventive method are functionally selective for the α5 subunit. In certain exemplary embodiments, the compounds are functionally selective for the α5 subunit as partial or full inverse agonists while substantially being antagonists at the α1, α2 and α3 subunits.

Functional selectivity can be shown by testing the compounds in whole cell patch clamp recordings from mouse fibroblasts stably expressing the human $GABA_A$ receptor subtypes, as reported by Chambers et al. [ref 11]. The in vitro efficacy can be measured as the percentage maximum modulation of the GABA-evoked current using a submaximal ($EC_{20}$) GABA concentration. Positive values represent a potentiation of the GABA-induced current (agonist) whereas negative values represent an attenuation (inverse agonist). Functional selectivity may also be shown by testing the compounds in cloned human α1, α2, α3 and α5-containing receptors transiently expressed in Xenopus oocytes by measurement of the modulatory effect on the GABA EC20 ion current using two-electrode voltage clamp electrophysiology (See Steinfeld et al. [ref 8])

The functional efficacy at the various receptor subtypes can be calculated using the method disclosed in WO 96/25948.

In certain embodiments, the compound's $EC_{50}$ at the $GABA_A$ α5 receptor subtype is at least 2-fold less, preferably at least 3-fold less, preferably at least 5-fold less, preferably at least 8-fold less, more preferably at least 10-fold less, more preferably at least 15-fold less, more preferably at least 20-fold less, than its $EC_{50}$ at the $GABA_A$ α1 α2 or α3 receptor subtypes.

Cognition Enhancement

In certain embodiments, compounds useful for carrying out the inventive method enhance cognitive function in subjects suffering from Down syndrome.

Cognition enhancement can be shown by testing the compounds in the Morris watermaze as reported by McNamara and Skelton, Psychobiology, 21:101-108. [ref 5]. It may also been tested by an object recognition test such that reported by Fernandez at al. [ref 3].

In certain embodiments, the compound produces cognition enhancing effects at an effective dose that correspond to a $GABA_A$ α5 receptor subtype occupancy between 25%±2% and 95%±2%, preferably between 25%±2% and 90%±2%, between 25%±2% and 80%±2%, between 25%±2% and 75%±2%, between 25%±2% and 70%±2%, between 25%±2% and 65%±2%, between 25%±2% and 60%±2%.

In certain embodiments, the compound produces cognition enhancing effects at a minimal effective dose that correspond to a $GABA_A$ α5 receptor subtype occupancy of 25%±2%.

Anxiogenic and/or Convulsant or Proconvulsant Side Effects

In certain embodiments, compounds useful for carrying out the inventive method does not exhibit measurable anxiogenic-like and/or convulsant or proconvulsant effects at doses that occupy >80%, preferably >90%, preferably >95% of benzodiazepine binding sites.

Anxiogenic and/or convulsant or proconvulsant potential can be shown by testing the compounds in assays measuring the potentiation of pentylenetetrazole-induced convulsions in mice. See, for example Chambers et al. [ref 11] for relevant experimental protocols.

3. Pharmaceutical Compositions

In another aspect, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

Thus, pharmaceutical compositions are provided which contain, as the active ingredient, one or more of the compounds described herein together with at least one pharmaceutically acceptable carrier, diluent or excipient. The pharmaceutical compositions are useful for treating or lessening the severity of cognitive impairments associated with Down syndrome, or for enhancing cognitive function in subjects suffering from Down syndrome.

In certain embodiments, the active pharmaceutical ingredient comprises at least one compound having inverse agonist functional selectivity for GABA$_A$ receptors containing the α5 subunit. In certain exemplary embodiments, at least one inverse agonist functionally selective for GABA$_A$ α5 receptor subtypes has one of the following structures:

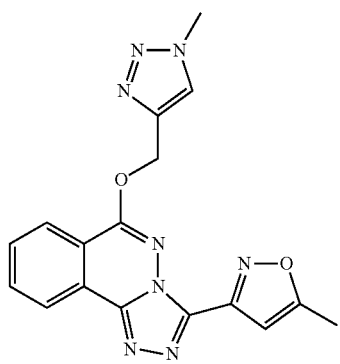

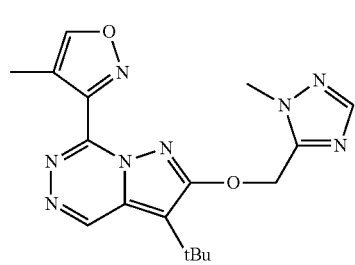

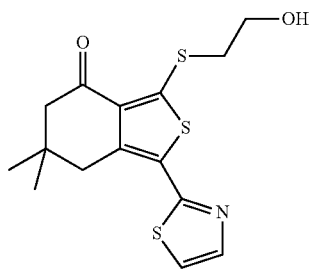

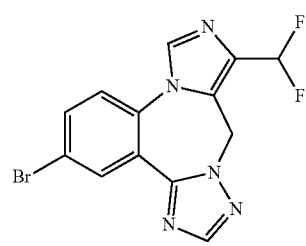

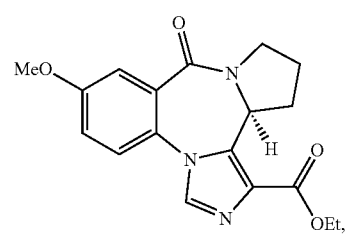

or pharmaceutically acceptable salt or prodrug thereof.

In certain exemplary embodiments, at least one inverse agonist functionally selective for GABA$_A$ α5 receptor subtypes has one of the following structures:

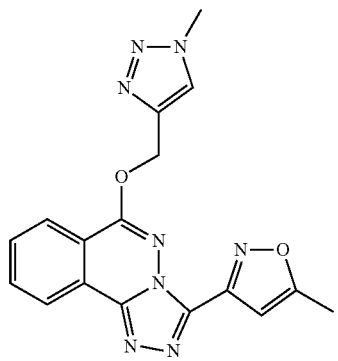

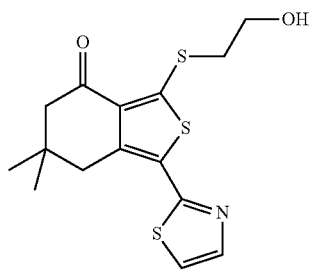

or pharmaceutically acceptable salt or prodrug thereof.

In certain preferred embodiments, at least one inverse agonist functionally selective for GABA$_A$ α5 receptor subtypes has the following structure:

or pharmaceutically acceptable salt or prodrug thereof.

In certain embodiments, the active pharmaceutical ingredient comprises at least one compound having both binding selectivity and inverse agonist functional selectivity for GABA$_A$ receptors containing the α5 subunit. In certain exemplary embodiments, at least one such compound has one of the following structures:

or pharmaceutically acceptable salt or prodrug thereof.

In certain preferred embodiments, a pharmaceutical composition is provided that comprises an effective amount of a compound having inverse agonist functional selectivity for GABA$_A$ receptors containing the α5 subunit, or pharmaceutically acceptable salt or prodrug thereof, in combination with a surfactant (surface-active agent or tension-active agent), for example polyethoxylated castor oil, as excipient and dimethyl sulfoxide as solvent. In certain embodiments, the composition is useful for treating or lessening the severity of cognitive impairments in subjects suffering from Down syndrome. In certain embodiments, the composition may be in the form of a gel capsule, or liquid solution or suspension. In certain embodiments, the composition may be a parenteral preparation. In certain embodiments, the parenteral preparation may be for an intravenous injection. In certain embodiments, the effective amount of the compound may be effective to produce a memory enhancing effect, a learning enhancing effect, or both. In certain embodiments, the composition may further comprise an additional therapeutic agent used for treating diseases or disorders associated with Down syndrome. The effective amount may be extrapolated from the classical dose-response curves, which allow the determination of EC$_{50}$ for a particular tested compound (the concentration of a drug which induces a response halfway between the baseline and maximum after some specified exposure time). The EC$_{50}$ of a graded dose response curve therefore represents the concentration of a compound where 50% of its maximal effect is observed. It is commonly used as a measure of drug potency and toxicity. For example, an effective amount for the compound α5IA may be between 3 and 10 mg per os, for example about 4 mg per os in humans.

In certain exemplary embodiments, the composition comprises at least one compound having one of the following structures:

-continued

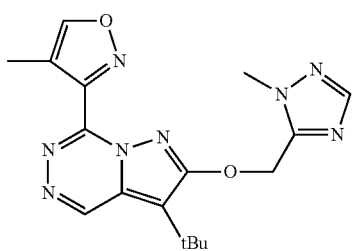

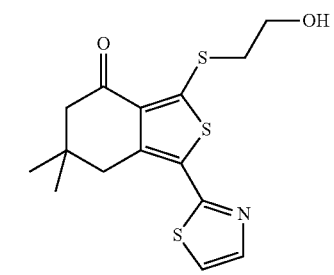

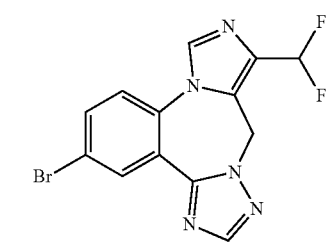

or pharmaceutically acceptable salt or prodrug thereof.

In certain exemplary embodiments, the composition comprises at least one compound having one of the following structures:

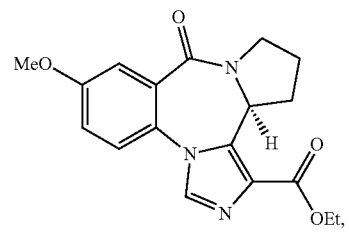

-continued

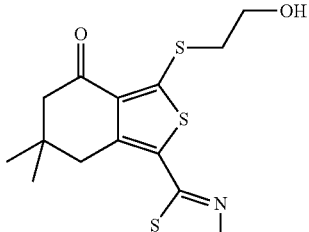

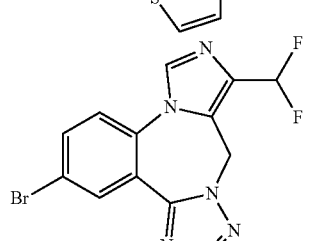

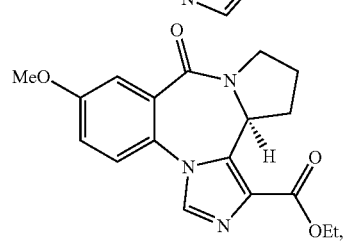

or pharmaceutically acceptable salt or prodrug thereof.

In certain preferred embodiments, the composition comprises at least one compound having the following structure:

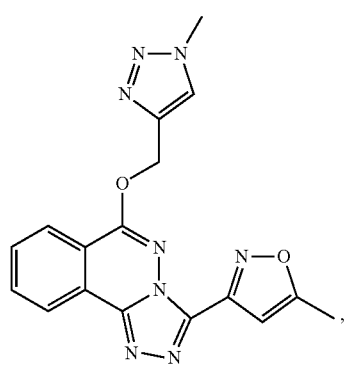 [SMILES: Cc1cc(-c2nnc3c4ccccc4c(OCc4cn(C)nn4)nn23)no1]

or pharmaceutically acceptable salt or prodrug thereof.

In certain exemplary embodiments, the surfactant is polyethoxylated castor oil. In certain exemplary embodiments, the polyethoxylated castor oil is Cremophor EL-H20®. Cremophor EL is the registered trademark of BASF Corporation for its version of polyethoxylated castor oil. It is prepared by reacting 35 moles of ethylene oxide with each mole of castor oil. The resulting product is a mixture (CAS number 61791-12-6): the major component is the material in which the hydroxyl groups of the castor oil triglyceride have ethoxylated with ethylene oxide to form polyethylene glycol ethers. Minor components are the polyethyelene glycol esters of ricinoleic acid, polyethylene glycols and polyethyelene glycol ethers of glycerol. In certain embodiments, other surfactants such as solutol HS15 may be used instead or in addition to the polyethoxylated castor oil.

In certain embodiments, the DMSO is used as co-solvent with water. In certain embodiments, the composition is formulated using a DMSO/polyethoxylated castor oil/water mixture where the polyethoxylated castor oil represents between 10 and 20%, preferably between 11 and 19%, preferably between 12 and 18%, preferably between 13 and 17%, preferably between 14 and 15%, preferably about 15% by volume of the DMSO/polyethoxylated castor oil/water mixture. In certain embodiments, the composition is formulated using a DMSO/polyethoxylated castor oil/water mixture where the DMSO represents between 5 and 15%, preferably between 6 and 14%, preferably between 7 and 13%, preferably between 8 and 12%, preferably between 9 and 11%, preferably about 10% by volume of the DMSO/polyethoxylated castor oil/water mixture. In certain exemplary embodiments, the composition is formulated using a ratio DMSO/polyethoxylated castor oil/water 5-15/10-20/65-85, preferably 5-15/10-20/68-82, preferably 6-14/11-19/70-80, preferably 7-13/12-18/72-78, preferably 8-12/14-16/73-77, preferably 9-11/14-16/74-76, for example Oct. 15, 1975. In certain embodiments, the compound is a hydrochloride salt of a compound having one of the following structures:

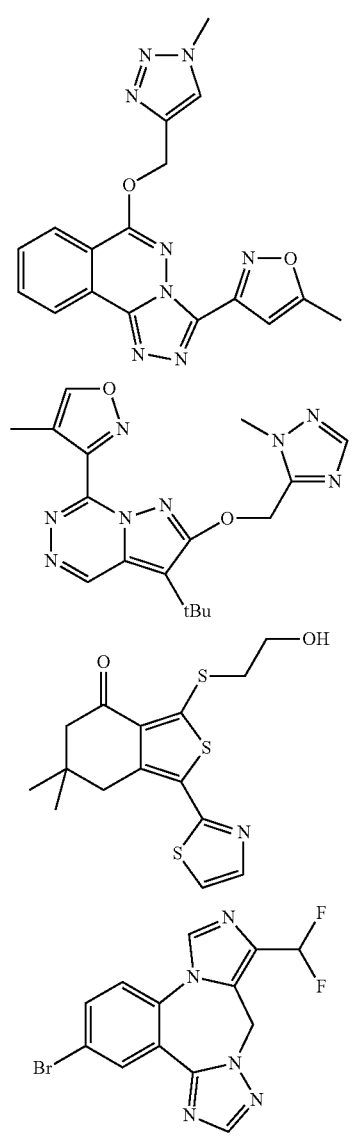

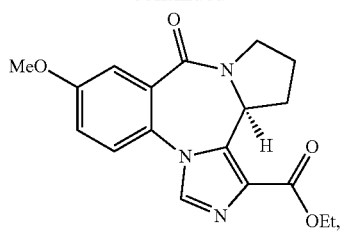

In certain exemplary embodiments, the compound is a hydrochloride salt of a compound having one of the following structures:

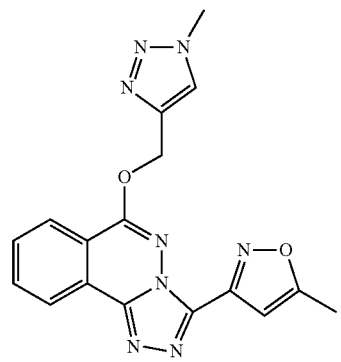

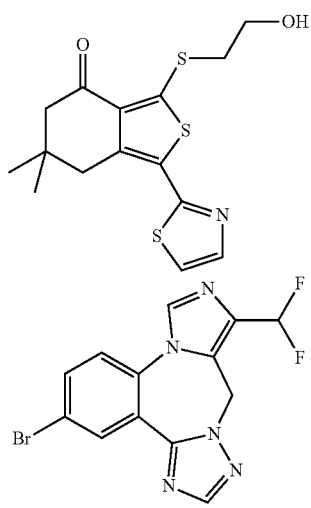

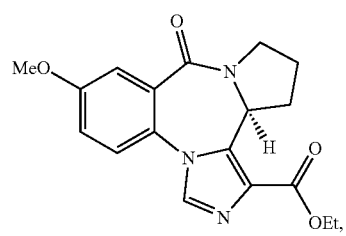

In certain preferred embodiments, the compound is a hydrochloride salt of a compound having the following structure:

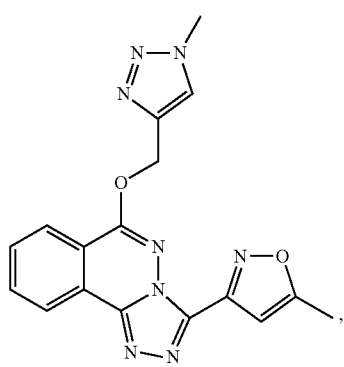 [SMILES: Cc1cc(-c2nnc3c4ccccc4c(OCc4cn(C)nn4)nn23)no1]

and the pharmaceutical composition further contains a surfactant (surface-active agent or tension-active agent), for example polyethoxylated castor oil, as excipient and DMSO as co-solvent. In certain embodiments, the surfactant is polyethoxylated castor oil and the composition is formulated using a DMSO/polyethoxylated castor oil/water mixture where the polyethoxylated castor oil represents between 10 and 20%, preferably between 11 and 19%, preferably between 12 and 18%, preferably between 13 and 17%, preferably between 14 and 15%, preferably about 15% by volume of the DMSO/polyethoxylated castor oil/water mixture. In certain embodiments, the composition is formulated using a DMSO/polyethoxylated castor oil/water mixture where the DMSO represents between 5 and 15%, preferably between 6 and 14%, preferably between 7 and 13%, preferably between 8 and 12%, preferably between 9 and 11%, preferably about 10% by volume of the DMSO/polyethoxylated castor oil/water mixture. In certain exemplary embodiments, the composition is formulated using a ratio DMSO/polyethoxylated castor oil/water 5-15/10-20/65-85, preferably 5-15/10-20/68-82, preferably 6-14/11-19/70-80, preferably 7-13/12-18/72-78, preferably 8-12/14-16/73-77, preferably 9-11/14-16/74-76, for example Oct. 15, 1975.

The inventive pharmaceutical composition based on the combination of DMSO as co-solvent and a surfactant (surface-active agent or tension-active agent), such as polyethoxylated castor oil, as excipient is proposed in view of the present investigators findings that a formulation α5IA.HCl in DMSO/Cremophor-EL®/water has improved effects as compared to known formulations of α5IA: 1) it allows better solubilisation of the active ingredient α5IA, and 2) it does not exhibit the unwanted side effects observed with the known formulations. In particular, the reported formulations (i.p. administration) are based on 70% PEG 300 and 30% water (Collinson et al. 2002 & 2006 [ref 12 and 13]), and induce a mortality rate as high as 10% in treated animals after an injection of 250 µL of formulation. See Example 4.

In contrast, with the inventive formulation based on α5IA hydrochloride salt, DMSO and a surfactant (surface-active agent or tension-active agent), such as polyethoxylated castor oil, no mortality is observed. In addition, in the resulting formulation, the crystals of active ingredient are smaller and more homogenous, reducing the risk of emboly consecutive to an i.v. injection.

The person skilled in the art will recognize that various active pharmaceutical ingredients set forth herein may be available in free base or salt forms, as enantiomerically pure stereoisomers and/or as polymorphs. Except as otherwise specified herein, recitation of a particular active pharmaceutical ingredient, without any qualification limiting the recitation to the free base or salt, enantiomer or polymorph of the active pharmaceutical ingredient, is intended to incorporate all the pharmaceutically acceptable forms of the active pharmaceutical ingredient, including the free base, pharmaceutically acceptable salts, racemate, enantiomerically pure formulations, amorphous and crystalline forms of the active pharmaceutical ingredient as well as their hydrates.

Different polymorphs of the compounds may also be used. Polymorphs are, by definition, crystals of the same molecule having different physical properties as a result of the order of the molecules in the crystal lattice. The polymorphic behavior of drugs can be of crucial importance in pharmacy and pharmacology. The differences in physical properties exhibited by polymorphs affect pharmaceutical parameters such as storage stability, compressibility and density (important in formulation and product manufacturing), and dissolution rates (an important factor in determining bio-availability). Differences in stability can result from changes in chemical reactivity (e.g. differential oxidation, such that a dosage form discolors more rapidly when comprised of one polymorph than when comprised of another polymorph) or mechanical changes (e.g. tablets crumble on storage as a kinetically favored polymorph converts to thermodynamically more stable polymorph) or both (e.g. tablets of one polymorph are more susceptible to breakdown at high humidity).

In certain embodiments, the compounds described herein or a pharmaceutically acceptable salt thereof are formulated in accordance with standard pharmaceutical practice as pharmaceutical composition for the therapeutic treatment (including prophylactic treatment) of mammals including humans.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

The active pharmaceutical ingredients, including pharmaceutically acceptable derivatives, pharmaceutically acceptable salts and polymorphic variations thereof, can be formulated as pharmaceutical compositions. Such compositions can be administered orally, buccally, sublingually, intravenously, parenterally, by inhalation spray, rectally, intradermally, transdermally, pulmonary, nasally or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term "parenteral" as used herein includes subcutaneous, intravenous, intramuscular, or intrasteraal injection, or infusion techniques. In some preferred embodiments the composition is administered orally, buccally or sublingually; in other preferred embodiments, the composition is administered intravenously.

The active pharmaceutical ingredients may be administered per se or in the form of a pharmaceutical composition wherein the active compound(s) is in admixture or mixture with one or more pharmaceutically acceptable ingredients, such as one or more carriers, excipients, disintegrants, glidants, diluents, delayed-release or controlled-release matrices or coatings. Pharmaceutical compositions may be formulated in a conventional manner using one or more physiologically acceptable carriers comprising excipients and auxiliaries, which facilitate processing of the active compounds into preparations which can be used pharmaceutically. Proper formulation is dependent upon the route of administration chosen.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975.

To prepare compositions, one or more compounds are mixed with a suitable pharmaceutically acceptable carrier. Upon mixing or addition of the compound(s), the resulting mixture may be a solution, suspension, emulsion or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action or have other action. The compounds may be formulated as the sole pharmaceutically active ingredient in the composition or may be combined with other active ingredients.

A solid carrier can be one or more substances, which may also act as diluents, flavoring agents, solubilizers, lubricants, suspending agents, binders, or tablet disintegrating agents; it can also be an encapsulating material.

In powders, the carrier is a finely divided solid, which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers include magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical composition may be in a coated form. Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

If oral administration is desired, the compound may be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Optional pharmaceutically acceptable excipients present in the drug-containing tablets, beads, granules or particles include, but are not limited to, diluents, binders, lubricants, disintegrants, colorants, stabilizers, and surfactants.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or non-ionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene mono laurate, polysorbates, polyoxyethylene octylphenylether, PEG-1000 cetyl ether, polyoxyethylene tridecyl ether, polypropylene glycol butyl ether, Poloxamer* 401, stearoyl monoisopropanolamide, and polyoxyethylene hydrogenated tallow amide. Examples of amphoteric surfactants include sodium N-dodecyl-[beta]-alanine, sodium N-lauryl-.beta.-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The active pharmaceutical ingredients may be complexed with other agents as part of their being pharmaceutically formulated. The pharmaceutical compositions may take the form of, for example, tablets or capsules prepared by conventional means with pharmaceutically acceptable excipients, such as binding agents (e.g., acacia, methylcellulose, sodium carboxymethylcellulose, polyvinylpyrrolidone (Povidone), hydroxypropyl methylcellulose, sucrose, starch, and ethylcellulose); fillers (e.g., corn starch, gelatin, lactose, acacia, sucrose, microcrystalline cellulose, kaolin, mannitol, dicalcium phosphate, calcium carbonate, sodium chloride, or alginic acid); lubricants (e.g. magnesium stearates, stearic acid, silicone fluid, talc, waxes, oils, and colloidal silica); and disintegrators (e.g. micro-crystalline cellulose, corn starch, sodium starch glycolate and alginic acid. If water-soluble, such formulated complex then may be formulated in an appropriate buffer, for example, phosphate buffered saline or other physiologically compatible solutions. Alternatively, if the resulting complex has poor solubility in aqueous solvents, then it may be formulated with a non-ionic surfactant such as TWEEN™, or polyethylene glycol. Thus, the active pharmaceutical ingredients and their physiologically acceptable solvates may be formulated for administration.

The liquid forms in which the pharmaceutical compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Liquid formulations for oral administration prepared in water or other aqueous vehicles may contain various suspending agents including synthetic and natural gums such as tragacanth, pectin, kelgin, carrageenan, acacia, alginates, dextran, sodium carboxymethylcellulose, methylcellulose, polyvinyl-pyrrolidone, polyvinyl alcohol and/or gelatin. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation by the patient.

Delayed release and extended release compositions can be prepared. The delayed release/extended release pharmaceutical compositions can be obtained by complexing drug with a pharmaceutically acceptable ion-exchange resin and coating such complexes. The formulations are coated with a substance that will act as a barrier to control the diffusion of the drug from its core complex into the gastrointestinal fluids. Optionally, the formulation is coated with a film of a polymer which is insoluble in the acid environment of the stomach, and soluble in the basic environment of lower GI tract in order to obtain a final dosage form that releases less than 10% of the drug dose within the stomach.

In addition, combinations of immediate release compositions and delayed release/extended release compositions may be formulated together.

The compounds may be prepared with carriers that protect the compound against rapid elimination from the body, such as time release formulations or coatings. Such carriers include controlled release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of such formulations are known to those skilled in the art.

It is anticipated that in some instances it may be advantageous to administer an active pharmaceutical ingredient of the invention as a pulsatile formulation. Such a formulation can be administered as a capsule, tablet or aqueous suspension. For example, a capsule, tablet or aqueous suspension may be formulated containing two or more populations of active pharmaceutical ingredient particle—one containing active pharmaceutical ingredient in an immediate release form (e.g. uncoated or coated with an immediate release coating) and another population in which the active pharmaceutical ingredient is coated with a delayed release coating and/or an enteric coating. In some embodiments, a pulsatile release of active pharmaceutical ingredient results in a longer-lasting formulation, which may be administered on a twice-a-day (b.i.d.) or once-a-day (q.d.) basis. In the case of a capsule, the two populations of particles maybe encased within an immediate release or delayed release capsule. In the case of a tablet (including a caplet) the two populations of particles may be compressed, optionally in admixture with an appropriate binder and/or disintegrants, to form a tablet core, which is then coated with an immediate release coating, an enteric coating or both. The tablet then may be coated with a coating that enhances the swallowability of the dosage.

In the case of a liquid suspension, the first population of particles may be uncoated (and indeed wholly or partially dissolved in the aqueous medium) or may be coated with an immediate release coating, an enteric coating or both. The second population of particles is coated with a delayed release coating and optionally an immediate release coating and/or an enteric coating. (Enteric coatings are generally applied where the active pharmaceutical ingredient is sensitive to low pH conditions and thus would be expected to be unstable in the stomach. They may also be applied to the delayed release population of particles in order to add an additional delay to the release of the active pharmaceutical ingredient within the delayed release particles.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as tween, or dissolution in aqueous sodium bicarbonate. Derivatives of the compounds, such as salts of the compounds or prodrugs of the compounds may also be used in formulating effective pharmaceutical compositions.

The active compound is included in the pharmaceutically acceptable carrier in an amount sufficient to exert enhancement of cognition in a subject suffering from Down syndrome in the absence of undesirable side effects on the subject treated (i.e., anxiogenic-like and/or convulsant or procinvulsant side effects). The therapeutically effective concentration may be determined empirically by testing the compounds in known in vitro and in vivo model systems as described herein.

The compositions can be enclosed in ampules, disposable syringes or multiple or single dose vials made of glass, plastic or other suitable material. Such enclosed compositions can be provided in kits.

The active materials can also be mixed with other active materials which do not impair the desired action, or with materials that supplement the desired action.

3. Treatment Kits

In another aspect, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

4. Methods of Use

In yet another aspect, the present invention provides a compound having inverse agonist functional selectivity for $GABA_A$ receptors containing the α5 subunit for use as a medicament for treating or lessening the severity of cognitive impairments in subjects suffering from Down syndrome. The invention also provides the use of a compound having inverse agonist functional selectivity for $GABA_A$ receptors containing the α5 subunit for the preparation of a medicament for treating or lessening the severity of cognitive impairments in subjects suffering from Down syndrome. Thus, there is provided a method for treating or lessening the severity of cognitive impairments in a subject suffering from Down syndrome, comprising administering to a subject in need thereof an effective amount of a compound having inverse agonist functional selectivity for $GABA_A$ receptors containing the α5 subunit, or an effective amount of a pharmaceutical composition comprising the compound, or pharmaceutically acceptable salt or prodrug thereof.

In another aspect, the present invention provides a compound having inverse agonist functional selectivity for $GABA_A$ receptors containing the α5 subunit for use as a medicament for enhancing cognitive function in subjects suffering from Down syndrome. The invention also provides the use of a compound having inverse agonist functional selectivity for $GABA_A$ receptors containing the α5 subunit for the preparation of a medicament for enhancing cognitive function in subjects suffering from Down syndrome. Thus, there is provided a method for enhancing cognitive function in a subject suffering from Down syndrome, comprising administering to a subject in need thereof a cognitive function enhancing amount of a compound having inverse agonist functional selectivity for $GABA_A$ receptors containing the α5 subunit, or a cognitive function enhancing effective amount of a pharmaceutical composition comprising the compound, or pharmaceutically acceptable salt or prodrug thereof.

In certain embodiments, the compound has one of the following structures:

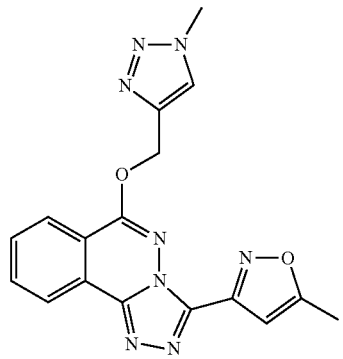

-continued

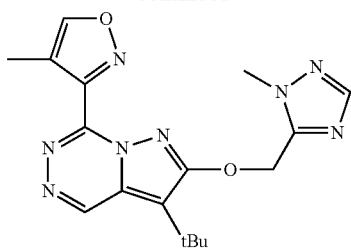

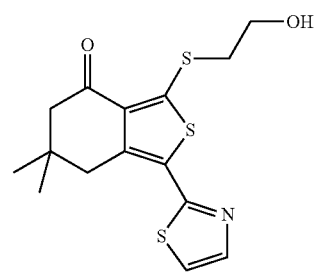

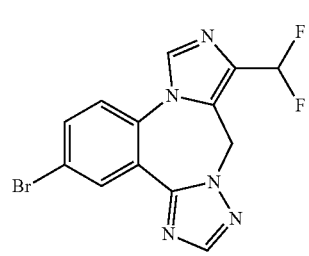

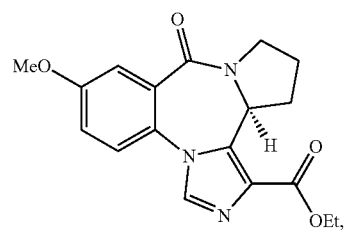

or pharmaceutically acceptable salt or prodrug thereof.

In certain exemplary embodiments, the compound has one of the following structures:

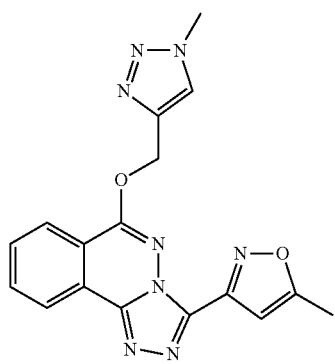

-continued

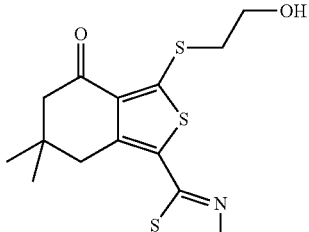

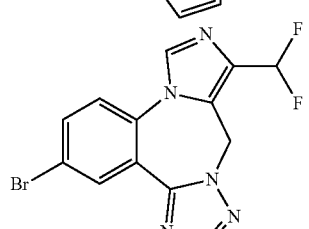

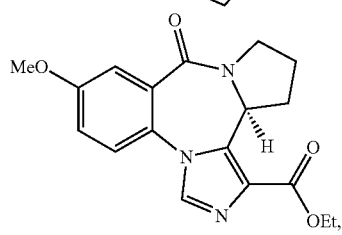

or pharmaceutically acceptable salt or prodrug thereof.

In certain exemplary embodiments, the compound has the structure:

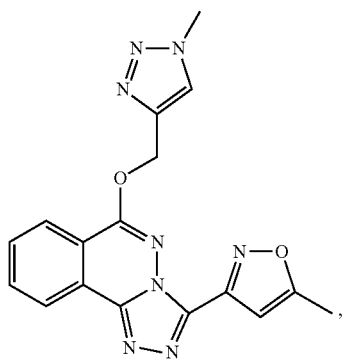 [SMILES: Cc1cc(-c2nnc3c4ccccc4c(OCc4cn(C)nn4)nn23)no1]

or pharmaceutically acceptable salt or prodrug thereof.

In certain embodiments, the compound is administered as an oral, buccal or sublingual pharmaceutical composition. In certain embodiments, the compound is administered in the form of a tablet, capsule, gel capsule, caplet or liquid solution or suspension. In certain embodiments, the compound is administered as a parenteral preparation. In certain embodiments, the parenteral preparation is for an intravenous injection. In certain embodiments, the effective amount of the compound is a sub-seizure inducing amount. Sub-seizure inducing amounts may be determined for example by measuring whether a convulsivant effect is observed at various amounts (doses) of compound. In certain embodiments, the compound may not have convulsivant effect at high % receptor occupancy (80-90%).

In certain embodiments, the effective amount of the compound is effective to produce a memory enhancing effect, a learning enhancing effect, or both. This may be determined by establishing dose-response curves by measuring the effect of the compound in a battery of neuropyschological tests in both mice and humans.

In certain embodiments, the compound is used in combination with an additional therapeutic agent used for treating diseases or disorders associated with Down syndrome.

The compounds and compositions, according to the method of the present invention, may be administered using any amount and any route of administration effective for treating or lessening the severity of cognition impairments in subjects suffering from Down syndrome. The exact amount required will vary from subject to subject, depending on the species, age, and general condition of the subject, the severity of the cognitive dysfunction, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the degree of cognitive impairment; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals by any appropriate route, for example, orally, rectally, parenterally, intracisternally, intravaginally, intraperitoneally, topically (as by powders, ointments, or drops), bucally, as an oral or nasal spray, or the like, depending on the severity of the infection being treated. Preferred modes of administration include oral and parenteral modes of administration.

The composition may be administered as a unit dosage forms of the type described above containing from 0.1 to about 500 mg of the active compound described herein. Typical unit dosage forms contain from 1 to 100 mg, for example 1, 2, 3, 4, 5, 10, 25, 50 or 100 mg, of the active ingredient. In certain embodiments, dosage forms may contain 3 to 10 mg of the active ingredient, for example about 4 mg.

For the enhancement of cognition, a suitable dosage level may be about 0.01 to 250 mg/kg per day, preferably about 0.01 to 100 mg/kg per day, preferably about 0.01 to 10 mg/kg per day, and especially about 0.01 to 5 mg/kg of body weight per day. The compounds may be administered on a regimen of 1 to 4 times per day, for example 1 to 2 times a day. In some cases, however, dosage outside these limits may be used. The therapeutic treatment may be carried out over a period of 2 to 12 weeks, for example for 4 weeks. In some cases, however, dosage regiment outside these limits may be used.

The active ingredient may be administered at once, or may be divided into a number of smaller doses to be administered at intervals of time. Alternatively, compounds of the invention may be administered continuously for a period of time, for example by an intravenous infusion or by means of a suitably placed transdermal patch incorporating and releasing compounds of the invention.

It is preferred that the compounds of the present invention are ground, for example using a pestle and mortar or industrial equivalent thereto, to a particle size of between 1 and 10 μM, and preferably less than 5 μM, before formulation. The compounds may be micronised or sonicised by methods known in the art or nanonised, for example by methods disclosed in U.S. Pat. No. 5,145,684.

In addition to the compounds of the present invention, the pharmaceutical composition of this invention may also contain, or be co-administered (simultaneously or sequentially) with, one or more pharmacological agents of value in treating one or more disease conditions referred to herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. Accordingly, the methods defined herein may be applied as a sole therapy or may involve, in addition to the compound of the invention, conventional chemotherapy. Such conjoint treatment may be achieved by way of the simultaneous, sequential or separate dosing of the individual components of the treatment. Such combination products may employ the compounds described herein.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to enhance cognitive function in Down syndrome subjects), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Medical Problems Associated typically with Down syndrome include congenital heart defects (e.g., Atrioventricular septal defects, Ventricular septal defect (VSD), atrial septal defect, or patent ductus arteriosus, Other complex heart disease such as Tetralogy of Fallot and hypoplastic left heart syndrome), pulmonary hypertension, problems with hearing (e.g., fluid buildup in the inner ear, ear infection or structural problems of the ear itself) and vision (e.g., congenital cataracts (loss of transparency of the lens of the eye), glaucoma (increased pressure within the eye), strabismus (cross-eyed) and major refractory errors (far sighted or near sighted), amblyopia (lazy eye)), intestinal abnormalities, seizure disorders, respiratory problems, obesity, an increased susceptibility to infection, leukemia (leukemia occurs in one of every 150 children with Down syndrome. This is 20 times higher than the general population), gastrointestinal abnormalities (2 percent to 5 percent of children have complete obstruction of the small bowel known as duodenal atresia. Another 2 percent have poor movement abilities of the colon and/or rectum known as Hirschsprung disease), and thyroid disorders.

Accordingly, in certain embodiments, the inventive method may include the co-administration (simultaneously or sequentially) of a compound or pharmaceutical composition of the invention together with an additional therapeutic agent appropriate for treating diseases or conditions associated with Down syndrome, such as those mentioned above.

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein.

The following examples contain important additional information, exemplification and guidance that can be adapted to the practice of this invention in its various embodiments and the equivalents thereof.

EXEMPLIFICATION

Summary

Treatment with $GABA_A$ antagonists can restore cognitive functions of Ts65Dn mice, a genetic model for Down Syndrome. Since these drugs are also convulsant, we evaluated safer therapeutic strategies using an inverse agonist (α5IA) selective for the α5 subtype-containing $GABA_A$-benzodiazepine receptors that inhibits GABAergic transmission without showing any convulsant activities. We demonstrate that α5IA alleviates learning and memory impairments in Ts65Dn mice by enhancing behaviorally-evoked immediate early gene products in the brain.

Down syndrome is the most common genetic cause of mental retardation (1/800 live births), and is characterized by varying degrees of cognitive impairments [ref 17]. Recent data suggest that changes associated with learning and memory dysfunction in DS might result, in part, from increased GABAergic inhibition in the brain, opening new avenues for therapeutic intervention [ref 2, 18]. The use of non-competitive $GABA_A$ antagonists can indeed restore impaired phenotypes in DS mice [ref 3, 19]. However, these drugs are convulsant at high doses, precluding their use, particularly in DS patients who may be more prone to convulsions [ref 9].

The goal of the present work was to assess the therapeutic potential of an α5-selective inverse agonist, the orally active 3-(5-methylisoxazol-3-yl)-6-[(1-methyl-1,2,3-triazol-4-yl)methyloxy]-1,2,4-triazolo[3,4-a]phthalazine [ref 8], referred to herein as compound α5IA, in cognitively-impaired Ts65Dn mice modeling DS [ref 1].

Figure 1:
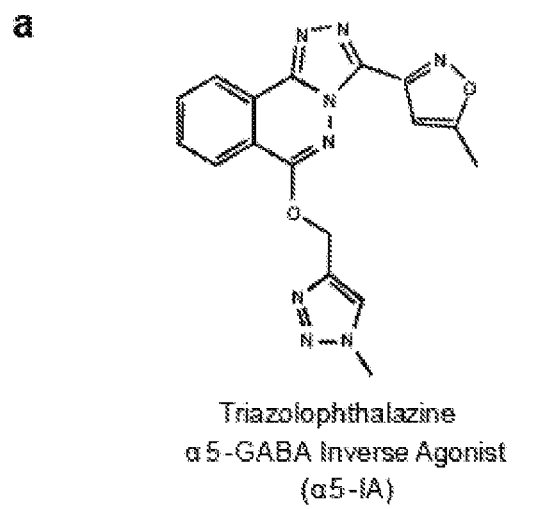
FIG. 1A depicts the structure of the triazolophthalazine α5-IA prepared by the method of Steinfeld and collaborators [ref 8] and used in this study as its hydrochloride salt. In the present document, this compound may be interchangeably referred to as α5IA, IAα5, α5-IA or IA-α5. In particular, the designation IAα5 or IA-α5 was used in the priority patent applications.
FIG. 1B depicts a 500 MHz $^1$H NMR spectrum of α5-IA taken in CDCl3.
FIG. 1C depicts results of an in vitro affinity study of α5IA for the benzodiazepine recognition site of the GABAA receptor compared to that of diazepam, given as IC50 and Ki molar values, as determined by displacement of [$^3$H]-flunitrazepam from rat whole brain tissue [ref 28]. Values are the average of three determinations.
Figure 1:
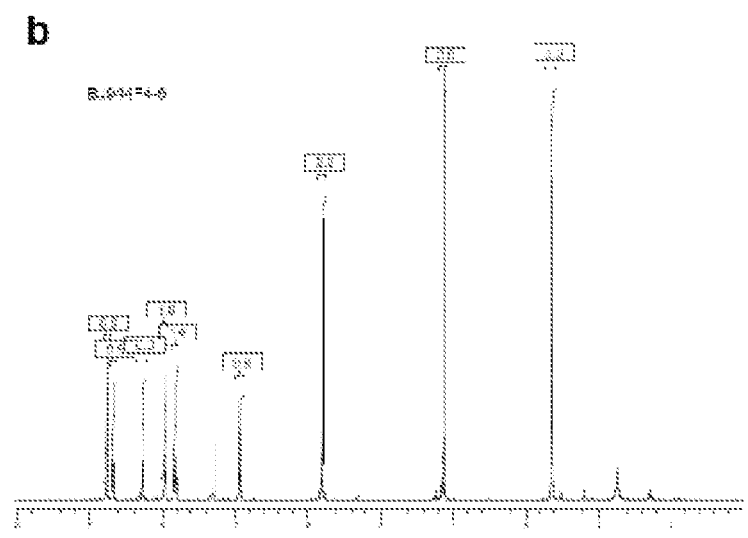
Figure 2:
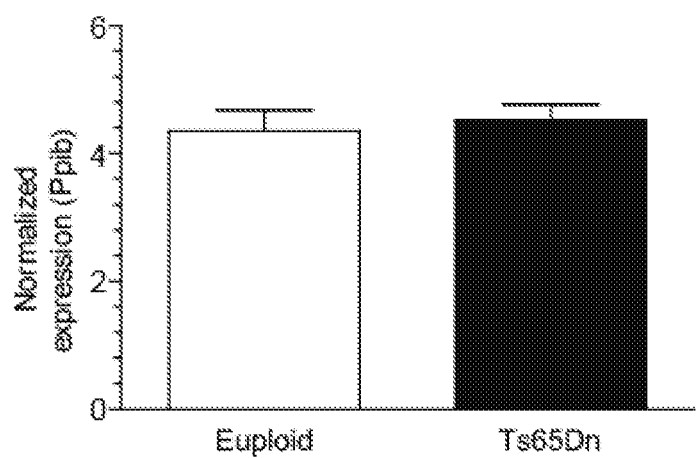
FIG. 2 shows that gene expression of Gabra5 is unchanged in Ts65Dn mice. Expression of the Gabra5 gene, encoding the α5-$GABA_A$ receptor subunit, was measured in the hippocampus of euploid and Ts65Dn mice using reverse-transcription/real-time quantitative PCR. Expression level of the Gabra5 gene was not different in Ts65Dn mice and in euploids (p>0.69).
Figure 3:
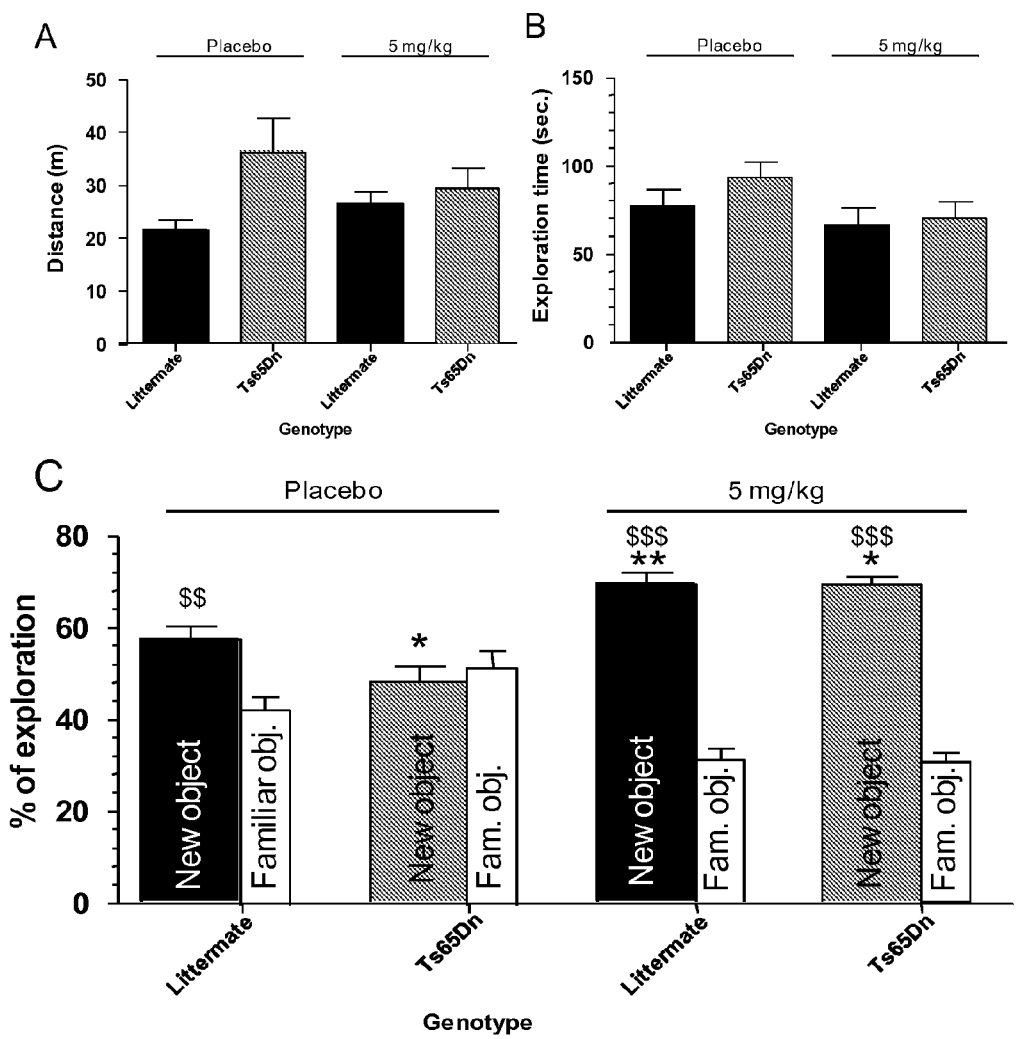
FIG. 3 depicts results of a study on the effect of α5IA treatment in Ts65Dn mice in an object Recognition test (See Example 2).
Figure 4:
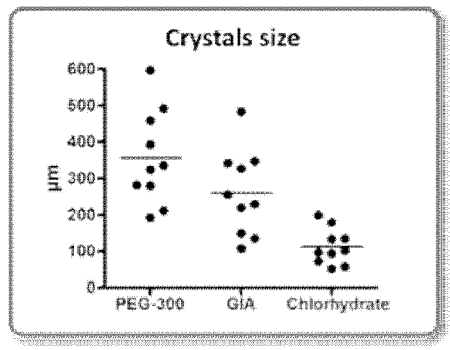
FIG. 4 depicts results of a comparative study on the effect of i.p. administration in mice of different formulations of α5IA. "GIA" stands for GABA Inverse Agonist, and represents the compound α5IA. (See Example 4).
Figure 4:
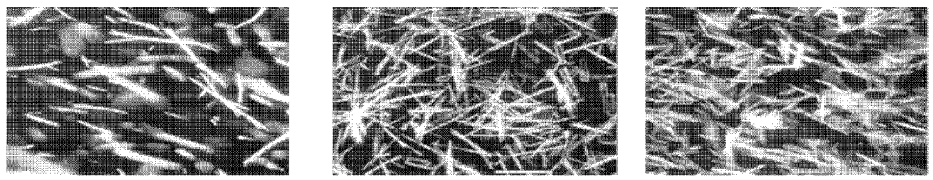
Figure 5:
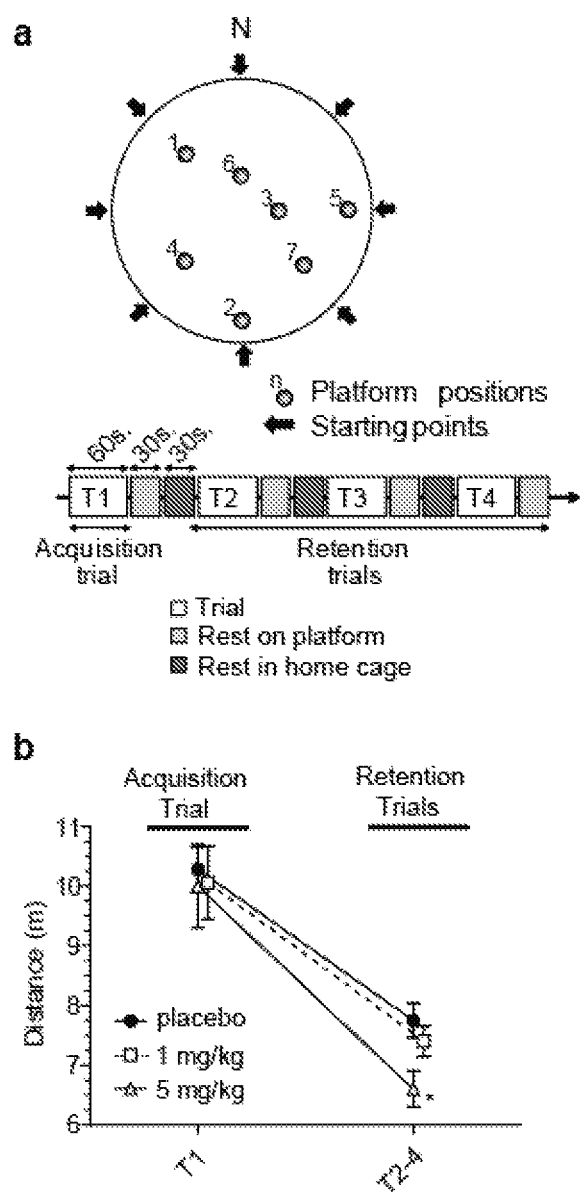
FIG. 5 depicts results from a dose-response effect study of α5IA. The optimal α5IA promnesiant dose was determined in mice trained in the DMTP task.
Figure 6:
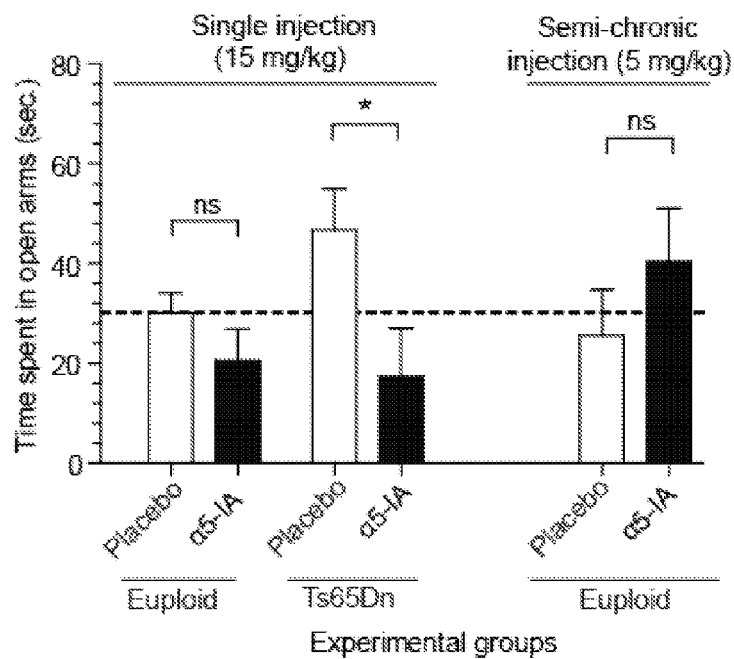
FIG. 6 depicts results from an anxiety-related behavior study of α5IA. Anxiety was assessed in the elevated plus maze, in both euploid and Ts65Dn mice under placebo or α5IA. Time spent in the open arms of the elevated plus-maze was taken as a measure of anxiety levels.

We first verified that the level of expression of the Gabra5 gene encoding for the α5 $GABA_A$ subunit was comparable in Ts65Dn and euploid mice (FIG. 2). We synthesized α5IA according to Sternfeld [ref 8] (FIG. 1) and selected the dose of 5 mg/kg i.p. to promote clear promnesiant effects in mice (FIG. 5) with no associated convulsant/pro-convulsant activity (See Example 3 and Table 1) nor anxiogenic and locomotor effects (FIGS. 6 and 7). Histopathological examination did not reveal any tissue alterations after chronic treatment with α5IA (FIG. 8 and Comments on FIG. 8). Given the absence of side effects of α5IA, we evaluated its therapeutic potential to rescue impaired cognition in Ts65Dn mice.

Spatial memory was assessed in the standard Morris water maze (MWM) task, in which mice swim in their environment to locate a hidden platform (FIG. 11A). α5IA or placebo was administered i.p. 30 min before each training session. While displaying normal visual abilities (FIG. 9), Ts65Dn mice under placebo were severely impaired as compared to euploid mice (p<0.0025), and displayed a delay to improve their hit performance across sessions (p<0.025) (FIGS. 11B & C). Treatment with α5IA decreased the use of inefficient search strategies by Ts65Dn mice (See Comments on FIGS. 9 & 10, and FIG. 10) and more importantly allowed them to regain normal learning performance (FIGS. 11B & C). Retention was evaluated during a single probe trial (no platform available). Memory for the target was demonstrated in euploid mice (p<0.05) but not in Ts65Dn mice, even after α5IA treatment (p>0.38) (FIG. 11D).

Non-spatial memory was assessed in the novel object recognition (NOR) task (FIG. 12A). Treatments were given 30 min before acquisition. Ts65Dn mice under placebo showed a memory impairment when compared to euploid mice (p<0.05). After α5-IA treatment, recognition memory was largely potentiated in both Ts65Dn and euploid groups (p<0.001) that displayed similar high retention performance (lack of genotype effect: p>0.99).

In parallel we performed a brain mapping analysis of the fos immediate early gene product ninety minutes after acquisition of the NOR task (FIGS. 12B and 13). Increased fos immunoreactivity was observed in euploid and Ts65Dn mice treated with α5IA as compared to mice under placebo. Notably, α5IA-induced increase of fos immunoreactivity was observed in different brain areas involved in recognition memory (e.g. perirhinal cortex) but not in the dentate gyrus, which contains only low levels of expression of the α5 subunit-containing $GABA_A$ receptors [ref 21].

In this study we demonstrated that Ts65Dn mice receiving a single administration of α5IA increased their cognitive performance in the NOR task. Furthermore, repeated α5IA treatment across training sessions in the MWM task allowed Ts65Dn mice to decrease their anomalous foraging behaviors, and to learn a fixed goal location with the same efficiency as euploid mice. α5IA, because of its lack of convulsant or anxiogenic effects, has a more favorable therapeutic profile than other GABAergic drugs ($GABA_A$ antagonists) and indeed has already been approved for studies in human subjects [ref 10].

Materials and Methods a. Animals

Mice were produced at the Intragene resource centre (TAAM, CNRS UPS44 Orléans, France) and bred on a mixed genetic background (B6C3<B>(1)) carrying a functional allele of Pd6b similar to that reported in Costa et al. [ref 24], thus avoiding the retinal degeneration and blindness phenotype in the engineered mice. For each experiment, different cohorts of naïve mice were used to avoid confounding effects of repeated testing. When transferred from one animal facility to the other, mice were acclimated to their new environment for at least 2 weeks before initiating behavioral experiments. The general health of mice was regularly checked, and body weights were assessed weekly throughout the experimental periods.

All experiments were conducted in accordance with the ethical standards of French and European regulations (European Communities Council Directive of 24 Nov. 1986). The supervisor of in vivo studies (B. Delatour) received official authorization from the French Ministry of Agriculture to carry out research and experiments on animals (authorization No. 91-282).

b. Real Time Quantitative PCR of Gabra-5

Expression of the Gabra-5 gene was studied using real-time quantitative PCR (qPCR) in 9 euploid and 7 Ts65Dn mice. Total RNA were extracted from the dissected hippocampi and treated with DNase using the Nucleospin RNA II kit (Macherey-Nagel, France). From each hippocampus, 500 ng total RNA was individually reverse-transcribed into cDNA overnight at 37° C. using the Verso cDNA kit (ThermoFisher Scientific, Waltham, USA) according to the manufacturer's instructions. The cDNAs were then diluted 1:20 for real-time qPCR amplification of the genes Gabra-5 and pPib (cyclophilin B) as reference gene (primers and probes were designed by the ProbeFinder software, http://www.universalprobelibrary.com)

qPCR assays were performed in a Lightcycler® 480 System (Roche), in the presence of 200 nM of each primer, 100 nM of specific hydrolysis probe and 1× Lightcycler® 480 Probes Master mix (Roche, France). Each reaction was performed in triplicate according to the manufacturer's instructions. Gabra-5 normalized expression values were calculated using the Lightcycler® 480 SW 1.5 software.

c. Statistical Analysis

Behavioral and morphological data were analyzed using parametric statistics, depending on the studied variables. In most cases, data were analyzed using an analysis of variance (ANOVA) with two factors: genotype (euploid vs Ts65Dn) and treatment (placebo vs α5IA). Statistical significance was set to a p value<0.05. All analyses were performed using Statistica v6 (StatSoft, Inc., Tulsa, Okla., USA) or GraphPad Prism (GraphPad Software, La Jolla, Calif., USA) software packages.

Note that to facilitate the presentation of the results, the ANOVA statistics have been presented using only p-values.

When not explicitly stated in figure legends, dependent variables have been plotted in each group as mean±standard error to the mean (SEM).

Example 1

Synthesis of Compound α5IA (714A3)

As used herein, the term "room temperature" refers to a temperature comprised between 20° C. and 25° C.

Compound α5IA (714A3) was obtained in 4 steps starting from 714A0 with an overall yield of 35.3%. These 4 steps were detailed below.

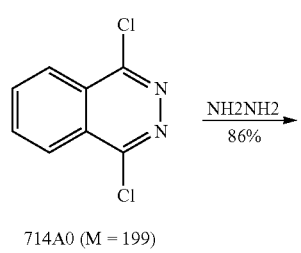

714A0 (M = 199)

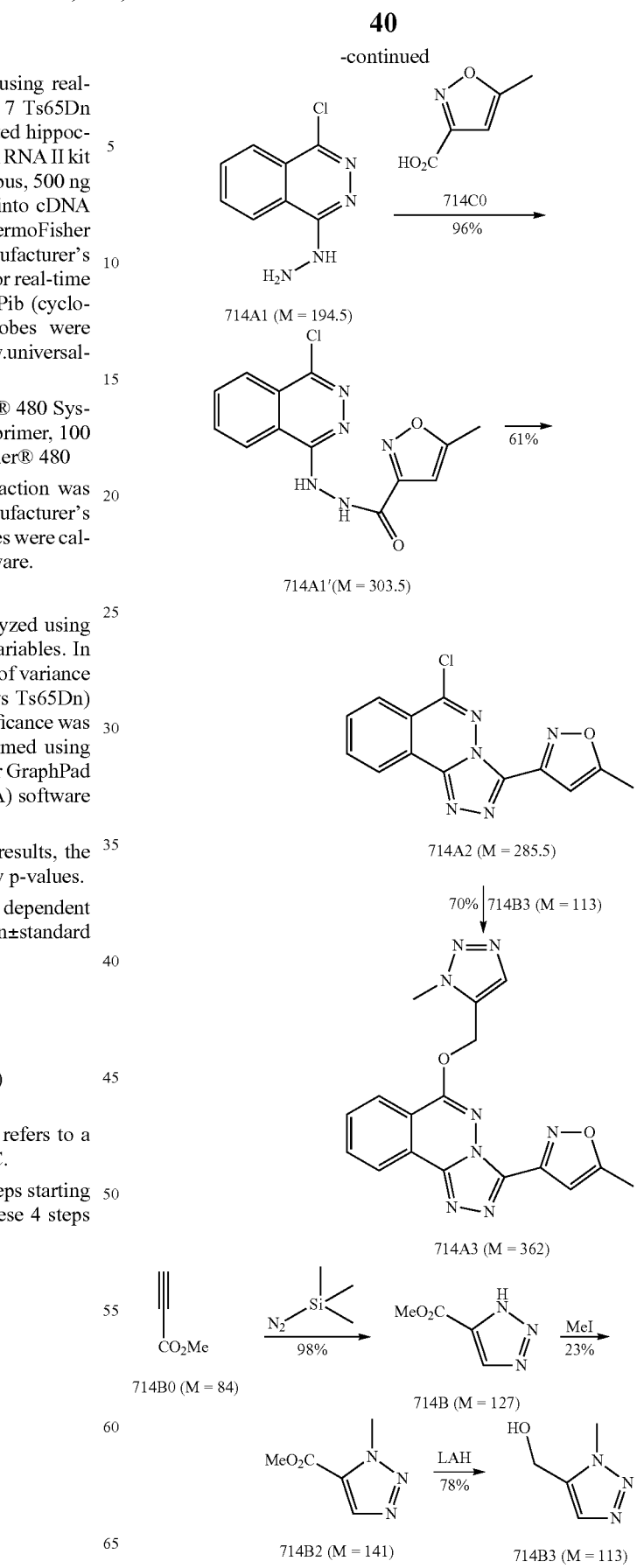

Step 1: Synthesis of Compound 714A1

Compound 714A0 (1 eq., 9.96 g, 50.1 mmol) was introduced in a 250 mL round-bottom flask. 106.4 mL of ethyl alcohol (36 eq., 1.80 mol), then 4.8 mL of ammonium hydroxide 20% (0.5 eq., 0.03 mol) were added under magnetic stirring. The mixture was heated to 60° C. Monohydrate hydrazine (3.6 eq., 0.18 mol, 9.0 g) was then added dropwise over 5 minutes. The resulting mixture was heated under reflux for 10 minutes (thick mixture, agitation was difficult). The mixture was then allowed to cool down to room temperature. The mixture was filtered, the flask was rinsed with a minimal quantity of ethyl alcohol. The filter was washed with water, ethyl alcohol and ether. After drying, 8.32 g of compound 714A1 were obtained as an off-white solid. The yield was 86%.

Step 2: Synthesis of compound 714A1'

$CH_2Cl_2$ (1051.6 mL, 383 eq., 16.34 mol), compound 714C0 (5.4 g, 1 eq., 0.04 mol), then triethylamine (11.8 mL, 2 eq., 0.09 mol) were introduced under argon in a 2 L reactor under mecanic stirring. The resulting mixture was cooled down to 0° C. under stirring, then bis(2-oxo-3-oxazolidinyl)phosphonic chloride (BOP—Cl, 10.9 g, 1 eq., 0.04 mol) was added. After stirring at this temperature for 45 minutes, compound 714A1 (8.3 g, 1 eq., 42.7 mmol) was introduced. The mixture was allowed under stirring at 0° C. for 2 hours then at room temperature over the night. The mixture was evaporated, taken up in water and filtered. The resulting solid was washed twice with water, then dried in rotavapor with ethyl alcohol. The solid was taken up and washed with pentane to provide compound 714A1' as a yellow solid (m=12.4 g). Yield: 96%.

Step 3: Synthesis of Compound 714A2

Triethylamine chlorhydrate (2.5 g, 0.4 eq., 0.02 mol), xylene (601.2 mL, 119 eq., 4.87 mol) then compound 714A1' (12.4 g, 1 eq., 40.9 mmol) were introduced in a 1 L three neck round bottom flask under magnetic stirring. The resulting mixture was heated under reflux for 3 hours, then allowed under stirring to room temperature over the night. DCM ($CH_2Cl_2$) was added to the resulting suspension so as to obtain a homogeneous mixture. The organic phase was washed with water, dried over $MgSO_4$, filtered and the solvent was evaporated. The residue was taken up in pentane to provide 8.39 g of a yellow solid. The solid was taken up for a DCM/$H_2O$ extraction. After the usual treatment, compound 714A2 was obtained as a yellow solid (7.1 g). Yield: 61%.

Step 4: Synthesis of Compound α5IA (714A3)

a) Synthesis of Reagent 714B3

Compound 714B3 was obtained in 3 steps starting from 714B0 with an overall yield of 17.6%. These 3 steps were detailed below.

Synthesis of Compound 714B1:

Compound 714B0 (24.9 mL, 1 eq., 0.298 mol) and $(CH_3)_3SiN_3$ were introduced in a 1 L autoclave under magnetic stirring. The resulting mixture was heated to 105° C. for 90 hours. The mixture was cooled down to 0° C., then 36 mL methanol were added dropwise. The mixture was stirred at room temperature for 45 minutes, then 20 mL ether were added. The solid was filtered, washed with ether, with pentane, then dried to provide an off-white solid (37.36 g). The solid was taken up in 80 mL of methanol. The resulting mixture was heated under reflux (solubilization), then ether was added until make the solution cloudy. The mixture was allowed without stirring and without heating for 2 hours. The resulting suspension was filtered, washed with ether to provide compound 714B1 as a white solid (28 g+9 g for the $2^{nd}$ lot). Yield: 98%.

Synthesis of Compound 714B2:

Compound 714B1 (27 g, 1 eq., 0.213 mol) then DMF (434.8 mL, 26.3 eq., 5.59 mol) were introduced in a 500 mL reactor under mecanic stirring. The resulting mixture was cooled down to 0° C. $K_2CO_3$ (35.21 g, 1.2 eq., 0.255 mol) was added by portion, then $CH_3I$ (31.7 g, 1.05 eq., 0.223 mol) was added dropwise. The mixture was stirred at 0° C. for 1 hour, then at room temperature over night. The solvent was evaporated; the residue was taken up in water and extracted with $CH_2Cl_2$. After drying and evaporating, the solid was taken up in $CH_2Cl_2$. The organic phase was washed with water and aqueous phases were re-extracted with $CH_2Cl_2$. The organic phases were gathered, dried over $MgSO_4$, filtered, then the solvent was evaporated. The resulting oil was taken up in ether and the resulting solid was filtered and washed with ether to provide 6.98 g of compound 714B2 as a white solid. Yield: 23%.

Synthesis of Compound 714B3:

Compound 714B2 (6.98 g, 1 eq., 49.5 mmol) and THF (tetrahydrofurane, 81.1 mL, 20 eq., 0.99 mol) were introduced in a 250 mL reactor under mecanic stirring. The resulting mixture was cooled down to 0° C. LAH (lithium aluminum hydride or $LiAlH_4$, 1.9 g, 1 eq., 0.05 mol) was added by portion. The mixture was stirred at 0° C. for 30 minutes, then at room temperature for 2 hours. The mixture was cooled down to 0° C., then hydrolysed with 2 mL of water, 2 mL of NaOH 15%, then 6 mL of water. After stirring at room temperature for 1 hour, the mixture was filtered, the salts were washed with THF, then the solvent was evaporated. The residue was taken up in $CH_2Cl_2$, dried over $MgSO_4$, filtered, then the solvent was evaporated to provide 4.34 g of compound 714B3 as a oil that crystallize. Yield: 78%.

b) Reaction Between Compound 714A2 and Reagent 714B3

Reagent 714B3 (2.8 g, 1 eq., 0.02 mol), then DMF (dimethylformamide, 665.2 mL, 344 eq., 8.55 mol) were introduced in a 2 L reactor under mecanic stirring. The resulting mixture was cooled down to −10° C. LiHMDS (lithium hexamethyldisilazide in tetrahydrofurane 1.06M, 26.9 mL, 1.1 eq., 0.03 mol) was added dropwise over 10 minutes. Le mixture was stirred at −10° C. for 50 minutes. Compound 714A2 (7.1 g, 1 eq., 24.9 mmol) in solution in 90.9 mL DMF (47 eq., 1.17 mol) was quickly added dropwise to the mixture. The mixture was allowed under stirring at room temperature for the night, then hydrolysed with water (450 mL, exothermic). The resulting suspension was filtered and washed with water. The resulting filter cake was dried in rotavapor (white powder: 7.4 g). Attempts to recrystallize the solid from $CHCl_3$ failed. The residue was purified by chromatography silica gel (eluant: DCM/AcOEt:5/5 then DCM/$CH_3OH$: 85/15) to provide compound α5IA (714A3) as a white solid (6.3 g). Yield: 70%.

Example 2

The Effect of α5IA on Ts65Dn Mice-Object Recognition Task

The testing protocol is a variant of the testing method according to Fernandez et al. 2007. The Object recognition protocol used to study learning and memory was performed on a 10 minutes period between the first presentation of the objects and the change of one object. Euploid and Ts65Dn mice were tested with or without α5IA treatment. The apparatus consisted of a black square arena (50×50 cm) located in a room under weak controlled luminosity (4-6 Lux) and constant 60 dB white noise. The first day, all mice (16 euploid and 16 Ts65Dn mice) were handled by the experimenter in the animal facility 2×3 min to familiarize them with human contact. On day 2, mice were placed for 20 min in the empty arena for getting used to the apparatus and test room. On day 3, four identical objects were placed symmetrically in the corners of the arena, 14 cm from the side walls. Mice were left for 20 min to explore the objects. On test day (Day 4), the mice were injected i.p. with either the placebo or the α5IA formulation before behavioural session (8 euploid and 8 Ts65Dn mice in each group). Thirty min after injections, mice were placed in the experimental apparatus containing two identical objects and were allowed to explore for 10 min. After this acquisition phase, mice returned to their home cage for a 10 min retention interval. To test short-term recognition memory, one familiar object (such as the one from the acquisition step) and one novel object were placed in the apparatus, and mice were placed for a second time in the chamber for 10 min to explore the two objects. Between each trial, objects were cleaned with 70° ethanol in order to reduce olfactory cues.

During all open field sessions, mice were monitored using a videotracking system (Any-Maze™). Object exploration was manually scored with an ethological keyboard and defined as the orientation of the nose to the object at a distance<6 cm. Sitting on the object was not considered as an object exploration.

For the retention phase, the percent of time exploring familiar vs. novel objects was calculated to assess memory performance (a score of 50% corresponding to equal exploration times of the two objects indicated no object memory). Note that one euploid and two Ts65Dn mice were removed from statistical analysis because they displayed abnormally low levels of object exploration during retention test (t<7 sec), precluding analysis of their memory performance. The remaining mice spent a large amount of time exploring objects (mean±SEM=77±12.9 sec).

Discrimination ratio was calculated using the formula:

$$I = \left(\frac{\text{Time (new object)}}{\text{Time (new object)} + \text{Time (familiar object)}}\right) \times 100$$

The effect of the benzodiazepine receptor inverse agonist functionally selective for the $GABA_A$ α5 receptor subtype, α5IA, on a murine model of Down syndrome was investigated using Ts65Dn mice. During the evaluation Ts65Dn and wild-type mice were tested for novel object recognition. Ts65Dn mice treated with α5IA had above-normal object recognition performance as compared to wild-type mice receiving a placebo. α5IA-treated Ts65Dn mice had object recognition performance similar to α5IA-treated wild-type mice.

Example 3

Study of Convulsant or Proconvulsant Effects of α5IA on Ts65Dn Mice

Comparison of β-CCM and α5IA

The convulsant action of the α5IA or beta CCM was evaluated after a single intraperitoneal injection of 50 or 3 mg/Kg of α5IA or beta CCM, respectively. The 50 mg/Kg dose of α5IA corresponded to 10 times the dose with promnesiant effects and 10 times the active dose in the object recognition test (5 mg/Kg)

For testing the pro-convulsant effects of α5IA, a sub-convulsant dose of pentylenetetrazole (45 mg/kg i.p.) that induces myoclonic convulsions in about 50% of mice was injected i.p. 20 min after injection of α5IA (50 mg/kg) or placebo.

The proconvulsant action of the α5IA was measured after injection of a subconvulsive dose of pentylenetetrazole. Mice were injected with either vehicle or the α5IA (50 mg/kg i.p) and 20 min later they received an intraperitoneal injection of 45 mg/kg of pentylenetetrazole. The animals were observed for 20 min (convulsant effects) or 50 min (pro-convulsant effects): the occurrence and latency to the first myoclonic jerk episode were recorded. Six to 7 mice were used for each condition. The latency to the first myoclonic jerk episode and the convulsion grade were recorded during a 1200-s period of observation. Four grades were empirically determined: Grade 0: no effect; grade 1: tail up and curved; grade 2: reversed tail and convulsive shivers; grade 3: myoclonic convulsions.

Neither euploid nor Ts65Dn mice displayed any convulsions after injection (see Table 1). We then tested the proconvulsant effect of α5IA by injecting it (50 mg/kg) 20 min before a sub-convulsant dose of pentylenetetrazol (45 mg/kg) that induces myoclonic convulsions in about 50% of mice. Injection of α5IA did not potentiate convulsant activity of pentylenetetrazol in either euploid or Ts65Dn mice.

TABLE 1

| Genotype | Treatment | Latency to myoclonic jerks | Convulsant mice rate |
|---|---|---|---|
| Convulsant effects | | | |
| Euploids | Placebo | / | 0/6 |
| | α5IA (50 mg/kg) | / | 0/6 |
| Ts65Dn | Placebo | / | 0/6 |
| | α5IA (50 mg/kg) | / | 0/7 |
| Pro-convulsant effects after pentylenetetrazol (45 mg/kg) | | | |
| Euploids | Placebo | 448.8 ± 145.5 | 4/6 |
| | α5IA (50 mg/kg) | 330.7 ± 90.21 | 3/6 |
| Ts65Dn | Placebo | 507.3 ± 39.77 | 3/6 |
| | α5IA (50 mg/kg) | 796.3 ± 354.0 | 4/7 |

α5IA (50 mg/kg) did not promote any convulsant effects, in either euploid or Ts65Dn mice.
The drug also did not modify the convulsant action of pentylenetetrazol (45 mg/kg) in the two genotypes.

Example 4

Improved Pharmaceutical Formulation Comprising α5IA as Active Ingredient

The effect of i.p. administration in mice of different formulations of α5IA was compared.

The physical properties of α5IA-PEG300/NaCl 9‰(7:3), α5IA-DMSO/Cremophor EL/water (10:15:75) and α5IA HCl salt DMSO/Cremophor EL/water (10:15:75) formulations were evaluated for viscosity (fluid (0) to very viscous (+++)), macroscopic aspect (solution or suspension), numbers of crystals (high density (+) or very high density (++)) and crystal size.

Biological impact of formulations were quantified regarding motor impairment (no motor effect (0)—important reduction of motor abilities (++)) and death rate after a 250 μL single injection.

|  | 0.6 µg/µL α5IA (free base) PEG-300/ NaCl 9‰ (7:3) | 0.6 µg/µL α5IA (free base) DMSO/ Cremophor EL/water (10:15:75) | 0.6 µg/µL α5IA HCl salt DMSO/ Cremophor EL/water (10:15:75) |
|---|---|---|---|
| Viscosity | +++ | 0 | 0 |
| Aspect | Opaque suspension | Opaque suspension | Opaque suspension |
| Presence of crystals | + | ++ | ++ |
| Crystal size | 356.9 ± 40.69 µm | 1 ± 36.91 µm | 112.6 ± 15.52 µm |
| Crystal homogeneity | − | − | ++ |
| Impact on motor skills 250 µL | ++ | 0 | 0 |
| Placebo mortality 250 µL | 10% | 0% | 0% |

Example 4

Dose-Response Effect of α5IA

To determine the optimal dose of α5IA, a dose-response study was performed in euploid mice trained in the delayed-matching-to-place task (DMTP), a classical learning and memory paradigm used to assess the promnesiant effects of drugs, and in particular of $GABA_A$ α5 inverse agonists [ref 8, 9, 11].

Experiments were performed in a Morris water maze (MWM). The maze was a 150-cm diameter pool filled with opacified water kept at 19° C. and equipped with a 9 cm diameter platform submerged 1 cm under the water surface. A total of 27 mice were used. Animals were randomly and equally distributed in 3 groups (placebo, α5IA 1 mg/kg, α5IA 5 mg/kg). Training was performed during 7 days. Animals were given four trials per session, and the position of the hidden platform was altered daily as described in FIG. 5-a, but remained constant within each session. Mice were injected with placebo or α5IA 30 min before the onset of behavioral testing. For each trial mice were released in the pool from a random starting point, and allowed to navigate until reaching the platform. The maximal trial length was 90 sec, after which mice were manually guided to the platform. Once on the platform, animals were given a 30 sec rest before being replaced in their home cage. At the end of a 30 sec inter-trial interval, mice were introduced de novo into the tank for the next trial using a new starting point. This procedure was repeated until four trials had been completed. Memory assessment was determined by comparing the distance to reach the platform on the first trial (acquisition trial) and the mean distance traveled in subsequent trials (retention trials).

Example 5

Locomotor Activity

Locomotor activity was evaluated in a total of 33 mice 30 min after i.p. injections (placebo: 8 euploid and 7 Ts65Dn mice; α5IA (5 mg/kg): 10 euploid and 8 Ts65Dn mice). Locomotion was measured in a square open field (50 cm×50 cm; luminosity: 30 lux) with black walls 30 cm high. Briefly, each animal was placed in the center of the arena and allowed to freely explore it for 10 min. Horizontal activity was monitored using the Any-Maze software. Time spent in the 10-cm wide peripheral zone and in the complementary 30 cm×30 cm central zone was recorded to evaluate anxiety.

Example 6

Anxiety-Related Behavioral Testing

Modulation of anxiety-related behaviors by α5IA was more precisely assessed using an elevated-plus maze, in a total of 42 mice, 30 min after i.p. injections (placebo: 11 euploid and 7 Ts65Dn mice; α5IA (15 mg/kg): 14 euploid and 10 Ts65Dn mice). The maze was constructed of black perspex (length, 28 cm; width, 5 cm; height from floor, 40 cm; overall luminosity in open arms: 70 1x) with two opposing open arms, and two enclosed arms equipped with three 16 cm high walls. Mice were placed in the central region of the maze and behavior was recorded for a 5 min period using the Any. Maze software that automatically calculates the time spent in the different parts of the maze (e.g., open and enclosed arms).

To explore the potential adversity of chronic injections of α5IA (5 mg/kg), another group of euploid mice was treated for two weeks (5 injections/week; 5 α5IA treated mice; 5 placebo-treated mice). After repeated treatment, these mice were evaluated in the elevated plus maze as described above.

Example 7

Anatomopathology after Chronic Treatment with α5IA

Mice treated for 2 weeks with α5IA and tested in the elevated plus maze were further treated for another 3 weeks. On the last day of treatment, urine samples were collected 2 hours after α5IA or placebo i.p. administration. Urine was stored at −20° C. before analysis. The day after, mice were injected i.p. with an overdose of sodium pentobarbital. Deeply anaesthetized mice received a PBS flush by means of an intracardiac perfusion. For anatomo-pathological examination, 3 additional euploid non-injected mice were also sacrificed. Liver, kidney, brain and spleen were dissected and fixed in a 10% formalin solution. Tissues were then paraffin-embedded and cut using a microtome (5 µm thick sections) before being processed for routine histopathological evaluation (hematein-eosin and Periodic acid-Schiff stainings).

Example 8

Morris Water Maze (MWM)

Spatial reference memory was evaluated using the standard Morris water maze task. The maze was similar to the one described above (dose-response effects of α5IA). The platform was submerged 1 cm below water surface in the center of one of the pool quadrants. During spatial allocentric training the non-visible platform remained at a constant position throughout the trials with numerous external visual indices available to facilitate formation of spatial cognitive maps.

A total of 32 mice (16 euploid and 16 Ts65Dn mice) were used. Animals were randomly and equally distributed into 4 groups. Each day mice were injected with placebo or α5IA (5 mg/kg) 30 min before the onset of behavioral testing.

On the first day, mice were submitted to a single habituation trial with the non-visible platform available. On the following six days, spatial allocentric training consisted in daily sessions (2 trials per session). Start positions varied pseudo-randomly among the four cardinal points. Mean inter-trial interval was 2 hours. During the habituation and spatial training phases each trial ended when the animal reached the platform. A 90 sec cut-off was used, after which mice were manually guided to the platform. Once on the platform, animals were given a 20 sec rest before being replaced in their cage. Twenty-four hours after the last training session, a probe trial was performed (Day 8) during which the platform was removed and mice allowed to freely navigate for 60 sec.

Following evaluation of spatial learning and memory skills, visual ability of mice was controlled using a non-spatial training procedure. Platform location was directly cued by a white styrene ball placed 12 cm above water surface and access to external indices was prevented by a black curtain surrounding the pool. Testing in this visually guided navigation task consisted of 4 daily sessions for 4 consecutive days as described above.

All data were collected, analyzed and stored using a video-tracking system (Ethovision, Noldus, Wageningen, The Netherlands).

Note that one Ts65Dn mouse was discarded from statistical analysis because it displayed abnormal floating behavior and decreased swim speed in the maze. During probe trial one supplementary (euploid) mouse was removed from analysis for the same reason.

Example 9

Measure of Cerebral Fos Immunoreactivity

The mechanism of action of α5IA was investigated by quantifying neuronal activity by measuring production of fos protein in mice subjected to an object recognition task (exploration of a new environment).

It is known that this protein, a transcription factor, is synthesized locally and rapidly in the brain at the level of neuronal populations activated by endogenous or exogenous stimuli. In particular, numerous literature data show that the c-fos gene coding for the fos protein is region-specifically expressed in animals during learning. The expression topography of c-fos varies depending on the type of learning, which stresses the specificity of the marker.

At baseline, the expression of c-fos is low throughout the CNS. It increases sharply following a stimulus, and does so in a specific fashion in certain brain regions, in agreement with the inducing agent. Fos protein can be detected by conventional immunohistochemistry and the resulting marking is nuclear. Its maximum concentration is approximately 2 h after stimulation and then decreases (Hoffman et al., 1993).

The protocol that was used involved treating mice (placebo or drug). 30 minutes later, the mice were subjected to exploring a new environment, a situation in which the animal acquires and stores information spontaneously. This behavioral stimulation activates c-fos gene, and the expression product of this gene (the Fos protein) is then detected by immunohistochemistry and quantified using dedicated image analysis software.

Four brain regions were examined in this study:
The field CA1 of the hippocampus (CA1),
The dentate gyrus of the hippocampus (GD)
The posterior cingulate cortex, also called cortical rétrosplénial granular (RSG),
The perirhinal cortex (PRH).

These four brain regions involved in processing mechanisms of sensory information and their memory.

Euploid (n=13) and Ts65Dn (n=6) mice were pseudo-trained in the object recognition task using the same protocol as described in the NOR task, but with no retention phase. Thirty min before acquisition, 6 euploid and 3 Ts65Dn mice were injected i.p. with α5IA (5 mg/kg). The remaining animals (7 euploid and 3 Ts65Dn mice) were injected with placebo. Following the open-field session, mice returned to their home cage. Ninety minutes following behavioral stimulation, mice were sacrificed with an overdose of sodium pentobarbital and perfused transcardially with PBS. Brains were extracted and fixed in 10% formalin for one week. After cryoprotection, brains were sectioned on a freezing microtome (40 μm frontal serial sections).

One series of sections was processed for fos immunodetection. Free floating sections were incubated with a primary anti-fos antibody (polyclonal AB-5, Calbiochem-VWR, France; dilution 1:10000) for 48 hours at 8° C. Subsequent steps were 1) incubation with secondary biotinylated goat anti-rabbit antibody (Sigma, France, 1:200), 2) reaction with avidin-biotin-peroxidase (ABC Vectastain standard kit, Vector Laboratories, Burlingame, USA, 1:400), 3) reaction with nickel-enhanced diaminobenzidine (Ni-DAB) forming gray/dark precipitates. Incubation time in Ni-DAB was the same for all mice.

Image analysis was performed as follows: regions of interest (ROIs) were photographed using an Olympus BX61 microscope (x10 objective) and fos immunostaining was quantified using a dedicated image processing software which automatically calculated the proportion of fos-stained tissue (p=stained area/total area), providing an unbiased stereological measurement of fos immunoreactivity. Four ROIs were analyzed: posterior cingulate cortex, perirhinal cortex, dentate gyrs and CA1 field of the hippocampus. Each ROI was sampled on several serial sections and results were then averaged to give a reliable quantitative evaluation of local fos immunostaining.

Example 10

Membrane Preparation and Binding Assay

The affinity of compounds at $GABA_A$ receptor subtypes may be measured by competition for [$^3$H]flumazenil (85 Ci/mmol; Roche) binding to HEK293 cells expressing rat (stably transfected) or human (transiently transfected) receptors of composition. α1β3γ2, α2β3γ2, α3β3γ2 and α5β3γ2.

Cell pellets are suspended in Krebs-tris buffer (4.8 mM KCl, 1.2 mM $CaCl_2$, 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets are resuspended in Krebs-tris buffer and homogenized by polytron for ca. 15 sec on ice. Protein is measured (Bradford method, Bio-Rad) and aliquots of 1 mL are prepared and stored at −80° C.

Radioligand binding assays are carried out in a volume of 200 μL (96-well plates) which contain 100 μL of cell membranes, [$^3$H]flumazenil at a concentration of 1 nM for α1, α2, α3 subunits and 0.5 nM for α5 subunits and the test compound in the range of $10^{-10}$–$3\times10^{-6}$ M. Nonspecific binding may be defined by $10^{-5}$ M diazepam and may typically represent less than 5% of the total binding. Assays are incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity may be detected by liquid scintillation counting. Ki values may be calculated using Excel-Fit (Microsoft) and are the means of two determinations.

Comments on FIG. 8: Solubility and Renal Toxicity of α5IA

Previous studies determined that α5IA is exclusively metabolized into the hydroxymethyl isoxazol metabolite M1 mainly in urine and in feces [ref 25]. M1 is poorly soluble in water and urine at room temperature, but its solubility increases in urine at 37° C. The effective promnesiant dose of α5IA in rats in the MWM test is 3 mg/kg (3-5). This dose corresponds to 80% receptor occupancy after 2 h and 60% after 8 h [ref 25]. The study that reported poor solubility of the M1 compound was performed after treating rats with a dose nearly 100 times higher (240 mg/kg) for 5 weeks [ref 26]. Induction of renal pyelitis and papillitis associated with crystals formation in the treated rats was reported in this study. However following chronic treatment with α5IA at a pharmacological dosage (5 mg/kg), we did not observe any histological abnormalities in different organs from the treated mice nor formation of abnormal crystals in urine (see FIG. 8). Furthermore, determination of the region of saturating concentration of M1 in urine was performed by adding solid M1 (3 mg) into urine [ref 25, 26]. This method does not however allow to study the solubility of α5IA and of its M1 metabolite in urine after peripheral administration (e.g. oral absorption). Given the poor solubility of M1, the chance of dissolution in urine is negligible.

While it displays poor solubility at very high doses, α5IA appears to be well tolerated in young and elderly subjects [ref 25]. Information has been previously provided on the dose that could be administered in clinical studies and on the duration of treatment with α5IA [ref 26]. The clinical trial on alcoholic syndrome performed by Nutt et al. [ref 10] used one single administration of 4 mg per os.

For Down syndrome clinical investigations using α5IA, the same type of protocol could be applicable. Alternatively, newly developed molecules showing inverse agonist profiles at the α5-$GABA_A$ receptors would also be suitable in the context of the present invention, especially as soon as they have been tested for innocuity in humans.

Comments on FIGS. 9 and 10: Spectrum of Action of α5IA on Learning and Memory in Euploid and Ts65Dn Mice.

Rescue of learning deficits in Ts65Dn mice by α5IA appeared to be specific. Thus, the cognitive defects α5IA counteracts were not due to either altered sensory functions in the MWM test (FIG. 9) or a decreased motivation to explore objects in the NOR task as the overall levels of object exploration were comparable in the two genotypes during NOR acquisition and test phases (ps>0.36). This emphasizes that α5IA primarily acts as a cognitive enhancer in the treated mice. In the low cognitive-demanding cued version of the MWM, we did not find any effect of α5IA (FIG. 8; p>0.16), thus reinforcing the hypothesis that α5IA targets only complex cognitive functions.

In the MWM test, we observed a strong effect of α5IA on the time spent in the 10-cm wide most peripheral annulus of the pool. This irrelevant thigmotactic behavior was strongly decreased after treatment with α5IA (FIG. 10). The effect was significant in Ts65Dn mice (p<0.001) but just failed to reach statistical significance in euploid mice (p=0.06), likely due to the fact that Ts65Dn mice displayed an overall increased basal level of thigmotaxy in comparison to euploid mice (p<0.0001). α5IA may directly potentiate learning skills and accordingly decrease the use of inadequate problem solving strategies (e.g., thigmotaxy). Alternatively, its action may first rely on the relief of irrelevant foraging behaviors with an indirect positive effect on acquisition performances.

Besides its therapeutic effects in Ts65Dn mice, α5IA also displayed a promnesiant action in euploid mice. The performance of euploid mice was significantly potentiated in the NOR test after treatment with α5IA.

As opposed to the DMTP test, the MWM task requires the animal to gradually memorize, throughout the trials and days, an invariant goal location. In this particular spatial reference memory paradigm, we noted that α5IA clearly facilitated the performance of Ts65Dn mice, but we did not observe a significant promnesiant effect of α5IA on learning performance of control euploid mice. This might suggest that the α5-IA promnesiant properties are both task- and genotype-dependent. However, this is not consistent qith data from other studies, which indicated that release of GABAergic inhibition using another less selective α5 $GABA_A$ inverse agonist (L-655,708) or a $GABA_A$ non selective antagonist (pentylenetetrazol) can facilitate acquisition in the reference memory water maze test, even in cognitively-normal wildtype rodents.

Finally, we evaluated the effects of α5IA on the retrieval of long-term (24 hours) spatial memories during the probe test of the navigation task. Our results indicate that α5IA did not significantly increase retention performance in either euploid or Ts65Dn mice, the latter animals remaining equally impaired following placebo or drug treatment. α5IA-treated Ts65Dn mice, while gradually increasing their learning proficiency across sessions to reach normal performance, did not demonstrate an adequate representation of the goal location as assessed by their poor retention performance during the probe trial. Our data might indicate that α5IA mainly exerts its nootropic action during the acquisition of information but is less potent in stimulating accurate retrieval of the previously formed memories. Alternatively, α5 $GABA_A$ inverse agonists could, in some circumstances, improve both the acquisition and the retrieval of spatial memories. However, these conclusions were obtained in memory paradigms based on short retention intervals (15-180 min) that did not fully allow assessing long-term (at least 24 hours) recall as usually performed during probe tests. From our data, it can be concluded that α5 $GABA_A$ inverse agonists promote learning performances and can even alleviate learning deficits in Ts65Dn mice, but that their action on the retrieval of long-term memories is more disputable and/or might be task-dependent.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

LIST OF REFERENCES

[Ref 1] Reeves et al., *Nature Genetics,* 11(2):177-84 (1995).

[Ref 2] Kleschevnikov et al., *The Journal of Neuroscience,* 24(37):8153-8160 (2004)

[Ref 3] F. Fernandez et al., "Pharmacotherapy for cognitive impairment in a mouse model of Down syndrome," *Nature Neuroscience,* 10:411-413 (2007).

[Ref 4] Lobaugh N J et al. Piracetam does not enhance cognitive abilities in moderate to high-functioning 7 to 13 year-old children with Down syndrome. Presented at the PAS/SPR meeting in San Francisco May 3, 1999; published in Archives of Ped and Adol Med, April 2001, 155 (4):442-448.

[Ref 5] McNamara and Skelton, *Psychobiology,* 21(2):101-108 (2002).

[Ref 6] Ballard et al., *Psychopharmacology,* 202:207-223 (2009).

[Ref 7] Atack et al., *Neuropharmacology*, 51:1023-1029 (2006).
[Ref 8] Sternfeld et al., *J. Med. Chem.*, 47:2176-2179 (2004).
[Ref 9] Dawson et al., *The Journal of Pharmacology and Experimental Therapeutics*, 316(3):1335-1345 (2006).
[Ref 10] Nutt et al., *Neuropharmacology*, 53:810-820 (2007).
[Ref 11] Chambers et al., *J. Med. Chem.*, 47:5829-5832 (2004).
[Ref 12] Collinson et al., *J. Neurosci.*, 22:5572-5580 (2002).
[Ref 13] Collinson et al., *Psychpharmacology*, 188:619-628 (2006).
[Ref 14] Venault et al., *Nature*, 321(6073):864-866 (1986).
[Ref 15] Schmitt et al. <<Neuro-modulation, aminergic neuro-disinhibition and neuro-degeneration. Draft of a comprehensive theory for Alzheimer disease>> *Med Hypotheses*. 2005; 65(6):1106-19. Epub 2005 Aug. 24.
[Ref 16] Palop et al. <<Aberrant excitatory neuronal activity and compensatory remodeling of inhibitory hippocampal circuits in mouse models of Alzheimer's disease." *Neuron*. 2007 Sep. 6; 55(5):697-711.
[Ref 17] Sherman, S. L., Allen, E. G., Bean, L. H. & Freeman, S. B. *Ment Retard Dev Disabil Res Rev* 13, 221-227 (2007).
[Ref 18] Best, T. K., Siarey, R. J. & Galdzicki, Z. *J Neurophysiol* 97, 892-900 (2007).
[Ref 19] Rueda, N., Florez, J. & Martinez-Cue, C. *Neurosci Lett* 433, 22-27 (2008).
[Ref 20] Sur, C., Quirk, K., Dewar, D., Atack, J. & McKernan, R. *Mol Pharmacol* 54, 928-933 (1998).
[Ref 21] Sperk, G., Schwarzer, C., Tsunashima, K., Fuchs, K. & Sieghart, W. *Neuroscience* 80, 987-1000 (1997).
[Ref 22] Siarey, R. J., Stoll, J., Rapoport, S. I. & Galdzicki, Z. *Neuropharmacology* 36, 1549-1554 (1997).
[Ref 23] S. M. Hoelter et al., *Front Biosci* 13, 5810 (2008).
[Ref 24] A. C. Costa, M. R. Stasko, C. Schmidt, M. T. Davisson, *Behav Brain Res* 206, 52 (2010).
[Ref 25] J. R. Atack, *Pharmacol Ther* 125, 11 (2010)
[Ref 26] S. A. Merschman et al., *Pharmazie* 60, 359 (2005).
[Ref 27] D. J. Moura et al., *Life Sci* 79, 2099 (2006).
[Ref 28] A. El Hadri, *J. Med. Chem.* 45, 2824-2831 (2002).
[Ref 29] Atack, J. R., Preclinical and clinical pharmacology of the GABA(A) receptor alpha5 subtype-selective inverse agonist alpha5IA. Pharmacol Ther. 2010 January; 125(1): 11-26.
[Ref 30] D'Hulst, C., Atack, J. R. and Kooy, R. F. (2009) The complexity of the GABAA receptor shapes unique pharmacological profiles. Drug Discov Today, 14, 866-875.
[Ref 31] Demas, G. E., Nelson, R. J., Krueger, B. K. and Yarowsky, P. J. (1996) Spatial memory deficits in segmental trisomic Ts65Dn mice. Behav Brain Res, 82, 85-92.
[Ref 32] Escorihuela, R. M., Fernandez-Teruel, A., Vallina, I. F., Baamonde, C., Lumbreras, M. A., Dierssen, M., Tobena, A. and Florez, J. (1995) A behavioral assessment of Ts65Dn mice: a putative Down syndrome model. Neurosci Lett, 199, 143-146.
[Ref 33] Hoffman, G. E., Lee, W. S., Smith, M. S., Abbud, R., Roberts, M. M., Robinson, A. G. and Verbalis, J. G. (1993) c-Fos and Fos-related antigens as markers for neuronal activity: perspectives from neuroendocrine systems. NIDA Res Monogr, 125, 117-133.
[Ref 34] Siarey, R. J., Carlson, E. J., Epstein, C. J., Balbo, A., Rapoport, S. I. and Galdzicki, Z. (1999) Increased synaptic depression in the Ts65Dn mouse, a model for mental retardation in Down syndrome. Neuropharmacology, 38, 1917-1920.
[Ref 35] US 2006/0084642
[Ref 36] WO 96/25948

The invention claimed is:

1. A method for treating or lessening the severity of cognitive impairments in subjects suffering from Down syndrome, comprising:
administering to a patient in need thereof a therapeutically effective amount of a compound having inverse agonist functional selectivity for $GABA_A$ receptors containing the α5 subunit, wherein the compound has one of the following structures:

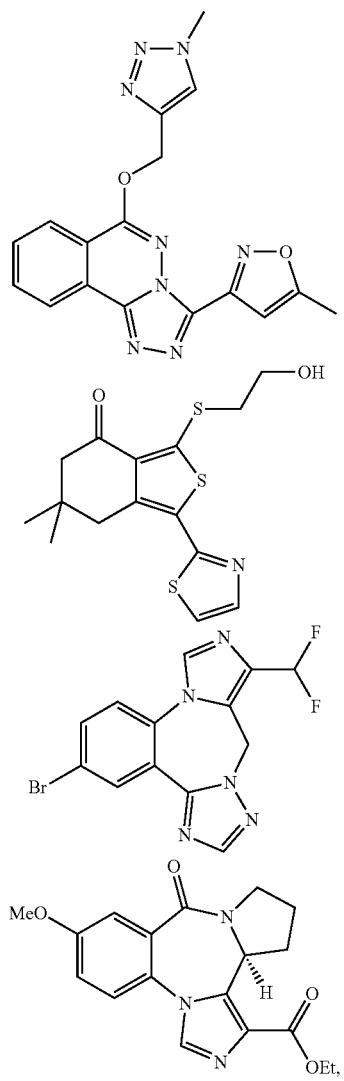

or a pharmaceutically acceptable salt thereof.

2. The method of claim 1, wherein the compound is administered as an oral, buccal or sublingual pharmaceutical composition.

3. The method of claim 2, wherein the compound is administered in the form of a tablet, capsule, gel capsule, caplet or liquid solution or suspension.

4. The method of claim 1, wherein the compound is administered as a parenteral preparation.

5. The method of claim 4, wherein the parenteral preparation is for an intravenous injection.

6. The method of claim 1, wherein the compound is a sub-seizure inducing amount.

7. The method of claim 1, wherein the compound is in an amount effective to produce a memory enhancing effect, a learning enhancing effect, or both.

8. The method of claim 1, wherein the compound is used in combination with an additional therapeutic agent for use as a medicament for treating diseases or disorders associated with Down syndrome.

9. The method of claim 1, wherein the compound is administered in combination with an excipient comprising a surfactant.

10. The method of claim 1, wherein the compound is administered in combination with a solvent comprising dimethyl sulfoxide.

11. The method of claim 1, wherein the compound is administered in combination with a surfactant and dimethyl sulfoxide.

* * * * *